United States Patent [19]

Lum et al.

[11] Patent Number: 5,701,901
[45] Date of Patent: Dec. 30, 1997

[54] ULTRASONIC PROBE WITH BACK AND FORTH SWEEPING ULTRASONIC SOURCE

[75] Inventors: Paul Lum, Los Altos; Carl Chang, El Cerrito; Jerry Zawadzki, San Jose, all of Calif.

[73] Assignee: Hewlett Packard Company, Palo Alto, Calif.

[21] Appl. No.: 756,385

[22] Filed: Nov. 26, 1996

[51] Int. Cl.$^6$ ..................................................... A61B 8/12
[52] U.S. Cl. ............................... 128/662.06; 128/662.03
[58] Field of Search .......................... 128/662.06, 660.1, 128/662.03, 660.08, 660.09

[56] References Cited

U.S. PATENT DOCUMENTS

| | | | |
|---|---|---|---|
| 4,794,931 | 1/1989 | Yock | 128/660.03 |
| 4,899,757 | 2/1990 | Pope, Jr. et al. | 128/479 |
| 5,000,185 | 3/1991 | Yock | 128/662.03 |
| 5,176,141 | 1/1993 | Bom et al. | 128/662.06 |
| 5,240,003 | 8/1993 | Lancee et al. | 128/662.06 |
| 5,271,402 | 12/1993 | Yeung et al. | 128/660.1 |
| 5,368,035 | 11/1994 | Hamm et al. | 128/662.06 |
| 5,497,782 | 3/1996 | Fugoso | 128/772 |
| 5,507,294 | 4/1996 | Lum et al. | 128/662.06 |
| 5,509,418 | 4/1996 | Lum et al. | 128/662.06 |
| 5,517,989 | 5/1996 | Frisbie et al. | 128/642 |
| 5,520,189 | 5/1996 | Malinowski et al. | 128/662.03 |
| 5,546,948 | 8/1996 | Hamm et al. | 128/662.06 |
| 5,606,975 | 3/1997 | Liang et al. | 128/662.06 |

OTHER PUBLICATIONS

Judy, et al., "Batch-Fabricated, Addressable, Magnetically Actuated Microstructures", Jun. 2–6, 1996, *Solid–State Sensor and Actuator Workshop*, Hilton Head, SC, pp. 187–190.

Tabata, O., "PH–Controlled TMAH Etchants For Silicon Micromachining", 1996, *Sensors and Actuators A*, 53, pp. 335–339.

Judy, et al., "Magnetic Microactuation of Polysilicon Flexure Structures", Dec. 1995, *J. Microelecromech. Sys.*, vol. 4, No. 4, pp. 162–169.

Judy, et al., "Fabrication Processes For Magnetic Microactuators With Polysilicon Flextures", Oct. 8–13, 1995, *4th International Symposium on Magnetic Materials, Processes and Devices*, Chicago, IL, 2–page paper.

Judy, et al., "Magnetic Microactuation of Torsional Polysilicon Structures", Jun. 25–29, 1995, *8th International Conference on Solid–State Sensors and Actuators*, Stockholm, Sweden, pp. 332–335.

Liu, et al., "A Micromachined Permalloy Magnetic Actuator Array for Micro Robotics Assembly Systems", Jun. 25–29, 1995, *8th International Conference on Solid–State Sensors and Actuators, and Eurosensors IX*, Stockholm, Sweden, pp. 328–331.

(List continued on next page.)

*Primary Examiner*—Marvin M. Lateef
*Assistant Examiner*—Derrick Fields
*Attorney, Agent, or Firm*—Philip S. Yip

[57] ABSTRACT

An ultrasonic probe for imaging tissues from inside a patient's body cavity is disclosed. The ultrasonic probe includes an end portion having a back and forth pivotable transducer assembly for transmitting an ultrasonic beam. The transducer assembly is supported by a silicon-containing support about a cavity and includes a transducer block on a base layer connected to the support via one or more twistable or flexible support arms. The transducer block includes a backing layer, a transducer layer on said backing layer, and an acoustic matching layer on the transducer layer. A bottom electrode in the transducer block penetrates the backing layer to connect electrically to a bottom face of the transducer layer to a conductor which is on a first face of the block. A top electrode penetrates the acoustic matching layer to connect electrically to a top face of the transducer layer to a conductor on a second face of the block for activating the transducer layer. The end portion also has an electromagnetic driver located near to the transducer assembly for acting on ferromagnetic material on the transducer assembly to result in pivotal motion of the transducer on the support arms.

25 Claims, 16 Drawing Sheets

OTHER PUBLICATIONS

Liu, et al., "Out-of-Plane Permalloy Magnetic Actuators for Delta-Wing Control", Jan. 29-Feb. 3, 1995, *Proc. IEEE Micro Electro Mechanical Systems*, Amsterdam, The Netherlands, pp. 7-12.

Garabedian, et al., "Microfabricated Surface Plasmon Sensing System", 1994, *Sensors and Actuators A*, 43, pp. 202-207.

Guckel, et al., "A First Functional Current Excited Planar Rotational Magnetic Micromotor", Feb. 7-10, 1993, *Proc. IEEE Micro Electro Mechanical Systems*, Fort Lauderdale, FL., pp. 7-11.

Ahn, et al., "A Planar Variable Reluctance Magnetic Micromotor With Fully Integrated Stator and Wrapped Coils", Feb. 7-10, 1993, *Proc. IEEE Micro Electro Mechanical Systems*, Fort Lauderdale, FL., pp. 1-6.

Richards, et al., "Surface-Plasmon Excitation Using a Polarization-Preserving Optical Fiber and an Index-Matching Fluid Optical Cell", Jun. 1, 1993, *Applied Optics*, vol. 32, No. 16, pp. 2901-2906.

Wagner, et al., "Microactuators With Moving Magnets For Linear, Torsional or Multiaxial Motion", 1992, *Sensors and Actuators A*, 32, pp. 598-603.

Pister, et al., "Microfabricated Hinges", *Sensors and Actuators A*, 1992, 33, pp. 249-256.

Ahn, et al., "A Fully Integrated Micromagnetic Actuator With a Multilevel Meander Magnetic Core", 1992, *IEEE*, 0-7803-0456-X/92, pp. 14-18.

Wagner, et al., "Microfabricated Actuator With Moving Permanent Magnet", 1991, *IEEE*, CH2957-9/91/0000-0027, pp. 27-32.

Tang, et al., "Electrostatic-Comb Drive of Lateral Polysilicon Resonators", *Sensors and Actuators*, 1990, A21-A23, pp. 328-331.

Steinbruchel, et al., "Mechanism of Dry Etching of Silicon Dioxide", *J. Electrochem. Soc.: Solid-State Science and Technology*, Jan. 1985, vol. 132, No. 1, pp. 180-186.

Sopori, "A New Defect Etch For Polycrystalline Silicon", Mar. 1984, *J. Electrochem. Soc: Solid-State Science and Technology*, vol. 131, No. 3, pp. 667-672.

Bergeron, et al., "Controlled Antisoptropic Etching of Polysilicon", Aug. 1982, *Solid State Technology*, pp. 98-103.

Mandurah, et al., "A Model for Conduction In Polycrystalline Silicon—Part 1:Theory", Oct. 1981, *IEEE Transactions on Electron Devices*, vol. ED-28, No. 10, pp. 1163-1170.

Bean, "Antisotropic Etching of Silicon", *IEEE Transactions on Electron Devices*, Oct. 1978, vol. ED-25, No. 10, pp. 1185-1193.

Declercq, "A New C-MOS Technology Using Antisotropic Etching of Silicon", Aug. 1975, *IEEE J. Solid-State Cir.*, vol. SC-10, No. 4, pp. 191-196.

Tenney, et al., "Etch Rates of Doped Oxides in Solutions of Buffered HF", Aug. 1973, *J. Electrochem. Soc.: Solid-State Science and Technology*, vol. 120, No. 8, pp. 1091-1095.

Kamins, et al., "Diffusion of Impurities in Polycrystalline Silicon", Jan. 1972, *J. Appl. Phys.*, vol. 43, No. 1, pp. 83-91.

van Gelder, et al., "The Etching of Silicon Nitride in Phosphoric Acid with Silicon Dioxide As a Mask", Aug. 1967, *J. Electrochem. Soc.: Solid-State Science*, vol. 114, No. 8, pp. 869-872.

Robbins, et al., "Chemical Etching of Silicon", Feb. 1960, *J. Electrochem Soc.*, vol. 107, No. 2, pp. 108-111.

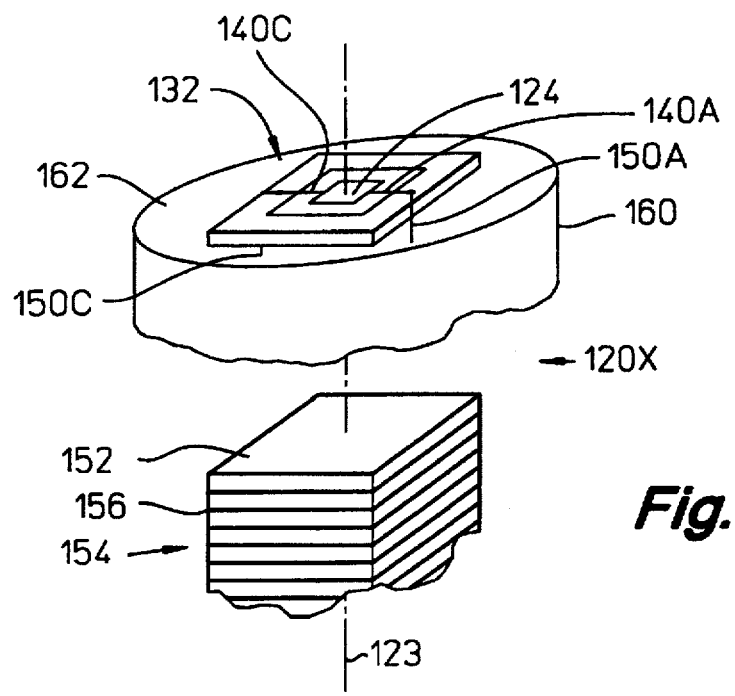
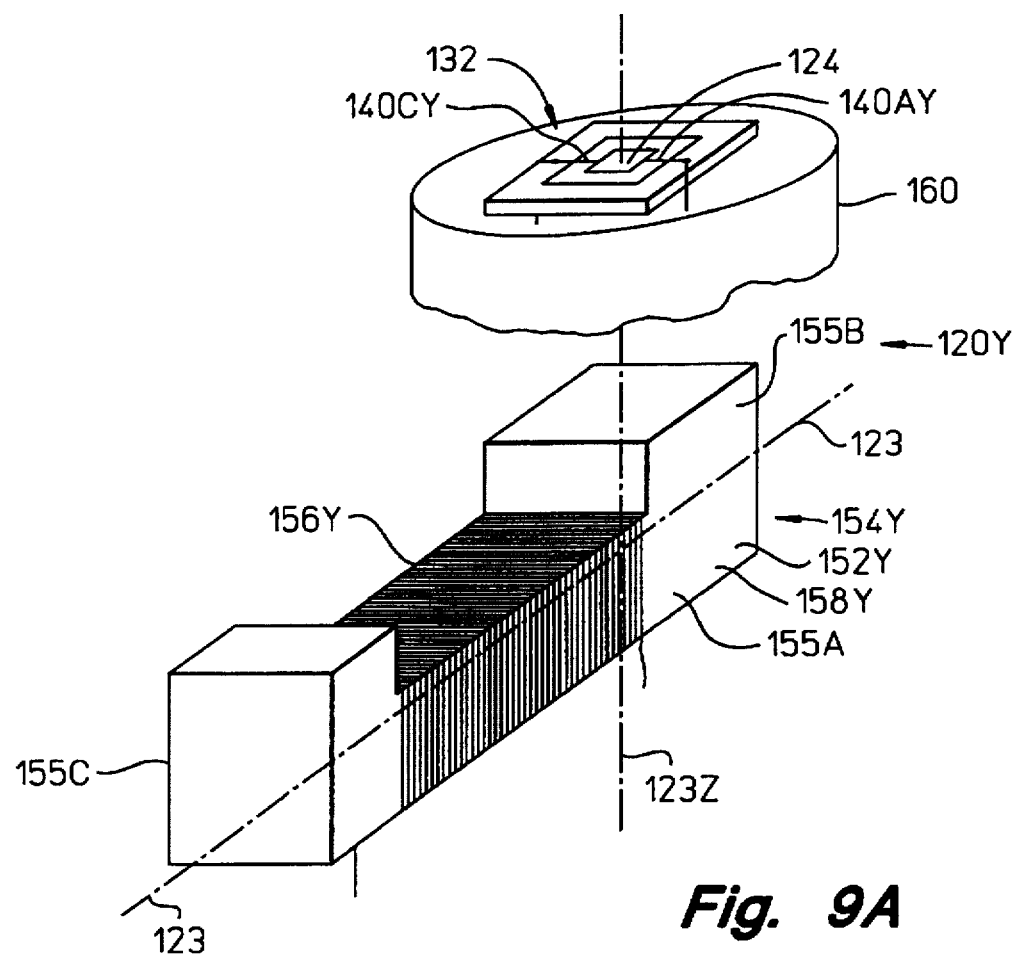

ULTRASONIC PROBE WITH BACK AND FORTH SWEEPING ULTRASONIC SOURCE

FIELD OF THE INVENTION

The present invention relates to imaging ultrasonic probes, more particularly, to intravascular imaging ultrasonic probes that scan tissues surrounding the probe by mechanically moving a transducer in the probe.

BACKGROUND

For many diseases, physicians have to access restricted areas in a patient's body. For example, a catheter may need to be inserted into a blood vessel for angioplasty or atherectomy. An ultrasonic probe that is insertable into the vessel would be useful to provide images so the medical worker can assess the condition of the vessel. A guidewire, over which the catheter can be slid, provides a means for introducing the catheter to the desired location. Preferably, the guidewire itself is also an ultrasonic probe because the body passageway, e.g., an artery, into which the guidewire is inserted, can be tortuous and the ability to image the surroundings as the guidewire is being inserted is beneficial for reducing trauma to the patient. An ultrasonic probe transmits an acoustic pulse into the body and detects the reflections of the pulse at tissue boundaries due to differences in acoustic impedance. The differing times taken for the transducer to receive the reflected pulse correspond to variations in the distance of the tissue boundaries from the ultrasonic source. By stepping, or sweeping, the ultrasonic probe through a selected angle, a two dimensional ultrasound image corresponding to a map of the acoustic impedance boundaries can be obtained. The intensity and position of the reflections from these boundaries will provide information on the condition of the body tissue being imaged.

In the literature, two types of ultrasonic probes have been described for diagnostic ultrasonic imaging. The first employs a synthetic aperture technique. For example, U.S. Pat. No. 4,917,097 (Proudian et al.) and U.S. Pat. No. 5,186,177 (O'Donnell et al.) teach how an ultrasonic beam is steered electronically from a transducer using the method of synthetic aperture. Generally, this involves the sequential excitation of selected elements in an array of transducer elements. The second scans by mechanical rotation of a means to direct acoustic pulses. The mechanically rotated type includes a few subclasses. In the first subclass, either the distal (remote from the operator) transducer or a mirror is rotated from the proximal end of the catheter by an extended drive shaft with a proximal motor (U.S. Pat. No. 4,794,931 (Yock) and U.S. Pat. No. 5,000,185 (Yock)). In the second subclass, the rotation is confined to the distal end, where either a miniature motor (U.S. Pat. No. 5,240,003 (Lancee et al.) and U.S. Pat. No. 5,176,141 (Bom et al.)) or a fluid driven turbine is used to rotate the transducer or the mirror (U.S. Pat. No. 5,271,402 (Yeung and Dias)). In a third subclass, a stationary proximal transducer is acoustically coupled to a rotating acoustic waveguide that conducts the sound to the distal end (e.g., U.S. Pat. No. 5,284,148 (Dias and Melton). In another subclass, e.g., U.S. Pat. No. 5,509,418 (Lum et al.), a turbine is rotated by an acoustic signal generated outside the vascular vessel to direct another ultrasonic signal in a rotating fashion. In yet another subclass, e.g., U.S. Pat. No. 5,507,294 (Lum et al.), an external driving member rotates a tube to rotate a reflecting element at the tip of the tube to reflect ultrasound.

Currently, the most widely used type of intracavity ultrasonic probe is the mechanically rotated system with a transducer having a single planar element placed at the distal end of the catheter. A reason for this preference is the superior image quality as compared with current synthetic aperture systems. However, the mechanically rotating ultrasonic probes have some shortcomings. For an ultrasonic probe with a drive motor proximal to the operator, i.e., remote from the transducer, a drive cable encircled by a sheath is generally needed to transfer mechanical energy to the tip of the catheter containing the transducer. A long cable may not transfer energy uniformly to the catheter tip to rotate the transducer or reflector uniformly. Furthermore, the probe is liable to fail over time because of the cable's rapid and repetitive rotation within the sheath. On the other hand, when a drive motor is located near the tip of the catheter, the motor must be small. Such fragile motors are electrically and mechanically complex, making them very expensive. With mechanical parts, e.g., ball bearings, etc., that undergo rigorous motion, the motor is liable to fail. Such motorized imaging mechanisms are not desirable for used in a small ultrasonic probe. What is needed is an ultrasonic probe with a structurally simple actuator at the tip of the probe for moving a transducer or reflector to scan tissues.

SUMMARY

The present invention provides an ultrasonic probe for imaging tissues from inside a patient's body cavity. The ultrasonic probe is elongated and has a distal end suitable for inserting inside the body cavity, whereas the proximal end of the ultrasonic probe is to remain outside the body.

The ultrasonic probe includes an elongated main body portion and an end portion connected distally to the elongated main body portion. The end portion has a back and forth pivotable transducer assembly for transmitting an ultrasonic beam. The transducer assembly is supported above a cavity by a silicon-containing support and includes a base layer connected to the support via one or more twistable or flexible support arms. In the support, a layer of ferromagnetic material is disposed on the base layer. A transducer block with generally flat faces and straight edges is disposed on the ferromagnetic layer. The transducer block includes a backing layer, a transducer layer, and an acoustic matching layer. A bottom electrode in the transducer block penetrates the backing layer to connect electrically the bottom face of the transducer layer to a conductor which is on one of the faces of the block. A top electrode penetrates the acoustic matching layer to connect electrically to the top face of the transducer layer to a conductor on another face of the block for activating the transducer layer. Each of these conductors on the faces of the block is electrically connected to a conductor on either one of the support arms. The support arms allow the pivotal motion of the transducer assembly to scan the ultrasonic beam at the wall of the body cavity for imaging. The end portion also has an electromagnetic driver for acting on the ferromagnetic material to result in the pivotal motion. The driver is located near the transducer such that all driving motions for driving the pivotal motion occur at the distal end of the ultrasonic probe.

The ultrasonic probe is made by a process that includes forming a generally rectangular transducer block, attaching the transducer block on a support slab, etching a cavity in the support slab such that the transducer block can pivot back and forth on one or more support arms over the cavity, and connecting the transducer electrically to an electromagnetic driver located proximate to the distal end of the ultrasonic probe such that all the mechanical motion for driving the back and forth pivotal motion of the transducer occurs at the distal end.

In a preferred process, the transducer block is made by dicing a large plate with a transducer layer sandwiched between a matching layer and a backing layer. Grooves (or channels) are cut on the matching layer and the backing layer in the large plate and filled with a conductive material such that the conductive material penetrates the matching layer and the backing layer to provide electrical conductivity to either faces of the transducer layer. Also, in a preferred embodiment, a single active (i.e., not ground) conductor can be used to provide activation energy to the transducer and driving energy to the electromagnetic driver.

In the ultrasonic probe of the present invention, a rotational cable is no longer needed to transfer rotational energy from the proximal end to the distal end of the ultrasonic probe as in the prior art devices. In fact, no energy needs to be transferred mechanically from the proximal end to the tip of the ultrasonic probe. Since the ultrasonic probe of the present invention can image tissues in a body cavity, for example, within a blood vessel, it can be advantageously inserted into a tortuous passageway with relative ease and safety. The imaging is done by scanning an acoustic beam of ultrasonic pulses over the tissues by a pivotal motion of a plate on which a transducer is affixed. As the plate pivots, for example, the transducer mounted on the plate, wobbles back and forth, thus sweeping the acoustic beam over a selected angle. Preferably, the plate pivots on a fulcrum at about the midpoint of the plate in a back and forth rocking (or see-sawing) manner. In the preferred apparatus the fulcrum is a torsion arm that is twistable to allow the plate to pivot. Therefore, no mechanical sliding, rolling, or frictional motion on a surface exists. This reduces the risk of failure of the ultrasonic probe.

Moreover, unlike motorized ultrasonic probes, the electromechanical system used to drive the pivotal motion in the present invention is relatively simple. No sophisticated stator and rotor mechanism is required at the distal end of the ultrasonic probe where the transducer is located. Therefore, a small driver, used for actuating the pivotal motion, can be fabricated with enhanced reliability for the ultrasonic probe. This will enable the fabrication of an ultrasonic probe usable in even small blood vessels or body cavities. Both forward-looking and sideward-looking transducers can be implemented in the same ultrasonic probe. This facilitates faster and less traumatic insertion into the body cavity.

It is contemplated that a non-guidewire ultrasonic probe can be made with the transducer assembly of the present invention. A small ultrasonic probe can be made to have forward-looking and sideward-looking transducers, if desired. This obviates the need for multiple instrument exchanges if both forward-looking and sideward-looking capabilities are required, thereby reducing the time needed for the imaging process and the trauma resulting from maneuvering the catheter within the body.

BRIEF DESCRIPTION OF THE DRAWINGS

The following figures show the embodiments of the present invention to better illustrate the apparatus of the present invention. In these figures, like numerals represent like features in the several views and the drawings are not drawn to scale for the sake of clarity.

FIG. 8 shows an exploded view in portion of the microactuator of an ultrasonic probe according to the present invention, showing an electromagnet.

FIG. 9A shows an exploded view in portion of the microactuator of another ultrasonic probe according to the present invention, showing an electromagnet.

DETAILED DESCRIPTION OF THE INVENTION

The present invention provides an ultrasonic probe and techniques for making it wherein the ultrasonic probe has an actuating mechanism proximate to the probe's tip, which is insertable into a patient's body. With the present technique, using chemical etching, a compact transducer assembly that pivots back and forth on supporting arms can be made. In a preferred embodiment, the conductors supplying power to the transducer are fabricated from ferromagnetic material and pivot with the transducer assembly on support arms in the presence of a magnetic field.

Figure 1:
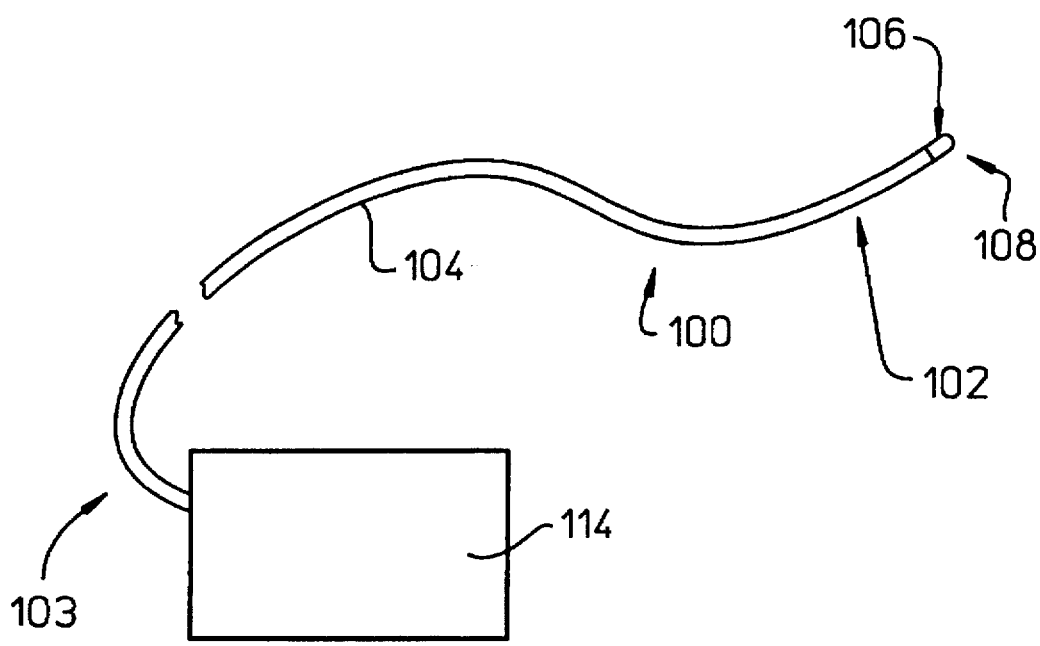
FIG. 1 shows a schematic representation of an ultrasonic probe according to the present invention.

FIG. 1 shows schematically an exemplary ultrasonic probe of the present invention, similar to that disclosed in application Ser. No. 08/657,742 (filed May 31, 1996 by Lum et al.), which is incorporated by reference in its entirety herein. The probe 100 has a distal end portion 102 for inserting into the patient's body cavity, e.g., an artery, and an proximal end 103 for the medical worker to control the operation of the probe. Between the distal end portion 102 and the proximal end 103 is an elongated main body 104. The elongated body 104 is connected to an "imaging head" 106 at the ultrasonic probe's distal end 108. As used herein, the term "distal" end of the ultrasonic probe refers to the end that can be inserted into a patient's body cavity, e.g., the lumen of a blood vessel. As used herein, the term "body cavity" refers to a hollow area generally surrounded by walls, although the hollow area is not necessarily entirely enclosed. Further, it is not limited to readily accessible cavities such as the oral cavity, the rectum, and the like. In the following description, a blood vessel is used as an example for the body cavity in which the ultrasonic probe can be used. However, it is to be understood that the present invention can be adapted for use in a variety of body cavities, such as a chamber in the heart, the esophagus, stomach, intestine, abdominal cavity, bladder, uterus, and the like.

Figure 2:
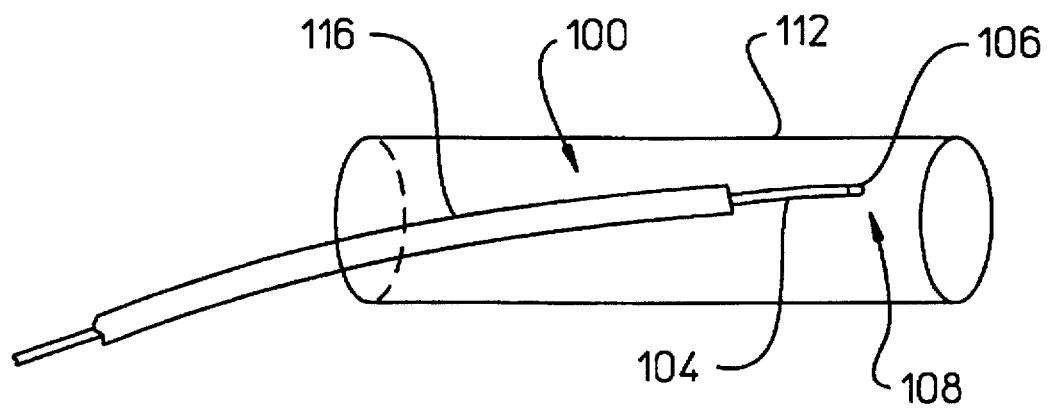
FIG. 2 shows a schematic representation of an ultrasonic probe according to the present invention, showing the probe being deployed in a blood vessel.

FIG. 2 shows how the ultrasonic probe 100 is deployed in a blood vessel 112. The imaging head 106 contains an ultrasound-emitting assembly which includes a transducer and the actuating mechanism for moving the transducer to scan an ultrasonic beam in the blood vessel 112. The ultrasonic beam is consisted of pulses. The proximal end 103, which is remote to the distal end 108, is electrically connected to an ultrasound controller 114 (see FIG. 1) that controls the emission and reception of ultrasound, as well as steering the ultrasound-emitting assembly. This controller 114 can also have the capability to analyze the electronic signals transmitted from the ultrasonic probe as a result of ultrasound signals received by the imaging head 106. Preferably, the controller 114 can further store and display data. In this case, computers, CRT monitors, and the like, can be present in the controller 114.

It is preferable that the proximal end 103 is detachable from the controller so as to facilitate inserting the probe to a desired position in the body cavity. An elongated sheath 116 is shown surrounding a significant portion of the elongated body 104 of the ultrasonic probe 100. Such a sheath, for example, can be inserted into the body cavity after the probe has been placed in the desired location. Such a sheath can be used for introducing various objects, e.g., angiographic catheter, pacing catheters, cutting tools for atherectomy, etc., into the body cavity. Instead of a sheath, structure 116 can also be, e.g., a catheter itself. It is contemplated that an imaging ultrasonic probe that is not a guidewire can be made, based on the present disclosure, by a person skilled in the art. Such a non-guidewire ultrasonic probe can be introduced by means of a sheath or a guidewire into the body cavity.

Figure 3A:
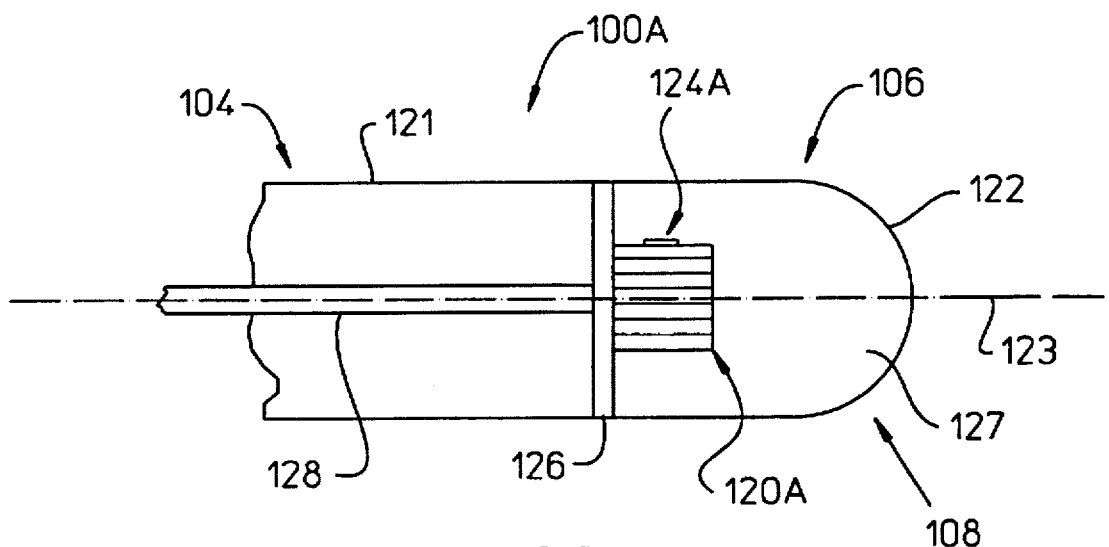
FIG. 3A shows a schematic representation of an embodiment of an ultrasonic probe according to the present invention.

FIG. 3A shows further details of a portion of an embodiment of the ultrasonic probe (labeled as 100A in FIG. 3A) at the distal end 108. In this embodiment, the elongated body 104 of the ultrasonic probe 100A has a tubular wall 121 connected to the imaging head 106. The imaging head 106 has a housing 122, for enclosing and protecting a microactuator 120A with a pivotable transducer assembly 124A for emitting and receiving ultrasonic signals. The housing 122 is substantially acoustically transparent (or sonolucent) to ultrasound emitted by the transducer assembly 124A. Alternatively, depending on the application, the housing 122 can have a window for emitting and receiving ultrasound. A support 126 is located proximal to and supports the microactuator 120A in rigid relation to the housing 122 and the wall 121, i.e., rigid except when the flexible nature of the wall is considered.

The ultrasonic probe has an imaginary center line extending longitudinally along the elongated body 104. The center line of the ultrasonic probe near the imaging head 106 is essentially a straight line and coincides with the longitudinal axis 123 of the distal portion of the ultrasonic probe 100A. The transducer 144 (see FIG. 6) is located laterally from the microactuator 120A. As used herein, "laterally" refers to a positional relationship in a direction radial to the axis 123 of the ultrasonic probe. A liquid 127 is contained in the housing 122. The liquid 127 matches the ultrasonic impedance of the housing 122 to reduce reverberations that damp the pivoting action of the microactuator 120A. The support 126 can also form a liquid-tight seal with the housing 122 to contain the liquid, although it can also be nonliquid-tight so as to allow infusion of fluid from the proximal end to the chamber defined by the housing 122. The transducer assembly 124A is generally planar and its normal points generally perpendicularly to the axis 123 of the ultrasonic probe 100A.

Figure 3B:
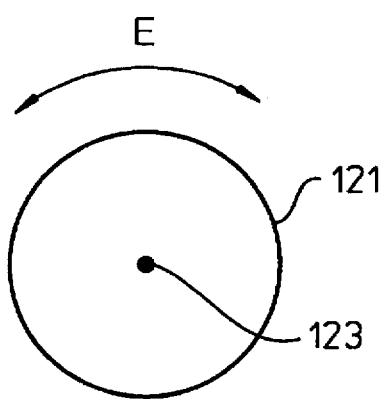
FIG. 3B is a schematic representation in axial view of the an embodiment according to FIG. 3A illustrating the direction of pivoting.
Figure 3C:
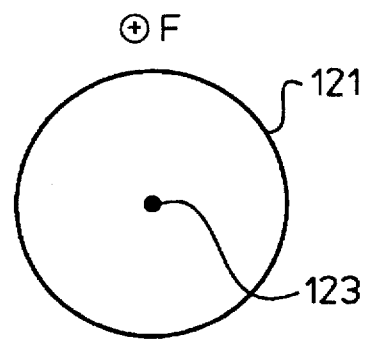
FIG. 3C is a schematic axial representation in axial view of the another embodiment according to FIG. 3A illustrating the direction of pivoting.

As the transducer assembly 124A emits an ultrasonic beam, the microactuator 120A rocks the transducer assembly 124A to sweep the ultrasonic beam in a plane perpendicular to the axis 123, as shown in FIG. 3B. The sweeping motion of the ultrasonic beam is shown by the two-headed arrow E. In an alternative embodiment, the transducer and the microactuator are arranged such that the ultrasonic beam sweeps out a plane parallel to the axis 123. The sweeping path of the ultrasonic beam is shown by the symbol ⊕, marked by F, going into the page in FIG. 3C.

The conductors for exciting the transducer on the transducer assembly 124A and the microactuator are located along a coaxial cable 128 inside the tubular wall 121 (see FIG. 3A). A relative stiff yet flexible core (not shown) inside the coaxial cable 128 is connected to the active potential to power the transducer. The outside conductor of the coaxial cable 128 can be connected to ground. The core contacts the support 126 for inserting and urging the probe into the body cavity, similar to the core of a typical guidewire. Alternatively, instead of the coaxial cable, wires separate from the cable can be used. The probe 100 has the usual structures that enables a guidewire to function well. For example, the tubular wall 121 of the guidewire includes coils to enable the guidewire to be flexible. Exemplary methods of making, methods of using, and structures of guidewires are described in, e.g., U.S. Pat. No. 5,517,989 (Frisbie et al.), U.S. Pat. No. 5,497,782 (Fugoso), U.S. Pat. No. 5,520,189 (Malinowski et al.), and U.S. Pat. No. 5,546,948 (Hamm et al.). The description on guidewires in these documents are incorporated by reference herein.

Figure 4:
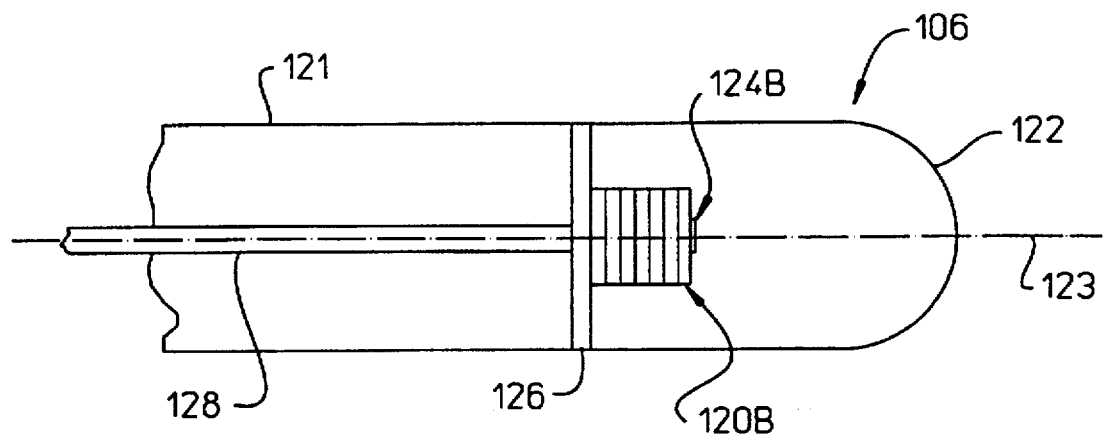
FIG. 4 shows a schematic representation of another embodiment of an ultrasonic probe according to the present invention.

In another embodiment of the ultrasonic probe of the present invention, the probe's distal portion is shown in FIG. 4, the transducer in the transducer assembly 124B is affixed distally to the microactuator 120B, thereby providing a way to scan axially, i.e., the scan angle can have a median generally along the axis 123 of the ultrasonic probe.

Figure 5:
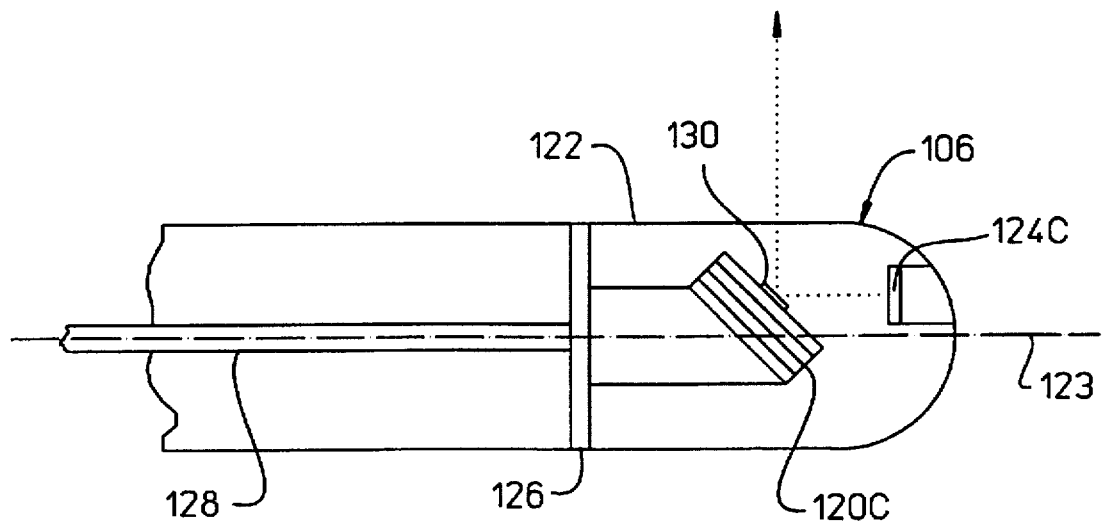
FIG. 5 shows a schematic representation of an embodiment of yet another ultrasonic probe according to the present invention.

In yet another embodiment of an ultrasonic probe, shown in FIG. 5, a transducer assembly 124C is supported proximate to the distal end 108 of the ultrasonic probe 100C along the probe's axis 123. A transducer 124C emits an ultrasonic beam axially toward the proximal end. The microactuator 120C and a pivotable reflector 130 are mounted at a slanted angle to the axis 123 of the ultrasonic probe such that the reflector reflects the axially-directed ultrasonic beam in a radial direction. As the reflector 130 pivots, it sweeps the ultrasonic beam to locations lateral to the ultrasonic probe 100C, thereby scanning the wall of the blood vessel 112 lateral to the ultrasonic probe.

Figure 6:
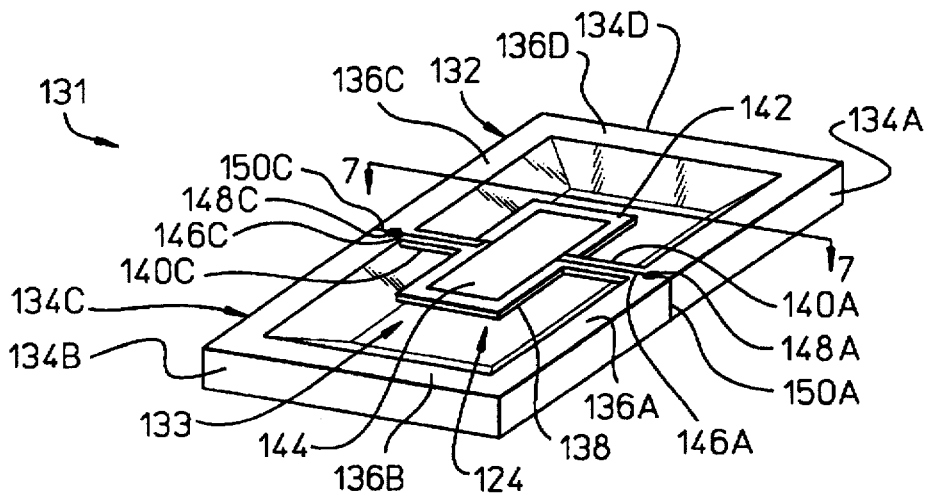
FIG. 6 shows an isometric representation of an embodiment of an ultrasonic probe according to the present invention, showing the transducer in a slab-shaped stage.
Figure 7:
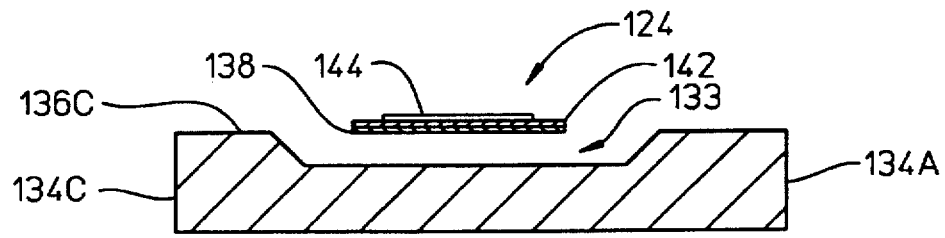
FIG. 7 shows a sectional view along line 7—7 of FIG. 6.

FIG. 6 shows a stage 132 of the ultrasonic probe according to the present invention in more detail. FIG. 7 shows a sectional view of the stage 132 along the line 7—7 in FIG. 6. In this embodiment, the stage 132 is generally slab-shaped. As used herein, the term "stage" refers to the structure that includes the substrate, plate, torsion arms, magnetic material, and the transducer, which will be described below. A cavity 133 in the stage 132 is surrounded by walls 134A, 134B, 134C, 134D, on which are ledges 136A, 136B, 136C, 136D. A generally rectangular plate 138 is supported on two opposing ledges 136A, 136C by two torsion arms 140A, 140C, located about the mid point of each opposite edge of the stage 132. A plate 138, whose thickness is much smaller than its other two dimensions, is balanced on the torsion arms 140A, 140C with the plate's center of gravity on an imaginary line joining the torsion arms. The torsion arms 140A, 140C are generally perpendicular to the thickness dimension. In this way, a minimal effort is needed to pivot, or turn, the plate on the torsion arms. If desired, the plate's center of gravity can be slightly off the torsion arms 140A, 140C without significantly affecting the performance of the ultrasonic probe. As used herein, the term "transducer assembly" refers to the structure including the plate, transducer, and magnetic material, if any. The terms "pivot" and "pivotal," when referring to moving the plate or transducer assembly, describe the turning motion about supporting arms that pivot or turn as if in a pivot. Therefore, the twisting motion on torsion arms, as long as the plate or transducer assembly is observed to turn or swing as if it is on a hinge or on a pivot, is considered to be "pivotal." Because the torsion arms 140A, 140C are affixed to the walls of the stage 132, the plate 138 pivotally moves in a rocking, back and forth fashion, thereby enabling a sweeping scan by the transducer affixed on the plate.

A ferromagnetic material 142, e.g., a nickel ferrite (herein referred to as "NiFe") material, is layered on a surface of the plate 138, covering generally all of that surface. In this way, when a varying magnetic field is applied to the plate, the plate will pivot on the torsion arms instead of trying to move up and down as a whole. Due to the ease of fabrication, preferably, the magnetic material 142 is layered on the upper surface of the plate 138. As used herein, the "upper" or "top" refers to a position that is distal from the cavity 133. If preferred, the magnetic material can be layered on the upper surface of the plate 138 on only one side of the torsion arms 140A, 140C, covering half of the surface before the transducer is affixed thereon.

The transducer assembly 124 includes the magnetic material 142 and a transducer 144 mounted on the upper surface of the plate 138. Electrical conductors 146A, 146C extend from transducer electrodes (not shown in the figures) to connection pads 148A, 148C. The connection pads 148A, 148C in turn can be connected to electrical conductors 150A, 150C to provide electrical energy to the transducer 144. Alternatively, one or more of the conductors 146A, 146C, 150A, 150C can be replaced by appropriately doped channels in the torsion arms and frame of the stage, i.e., stage 132. The electrodes are connected to the surfaces of the transducer 144 to electrically generate and receive ultrasound by the piezoelectric effect. As the transducer 144 is excited and the plate 138 is pivoted by a varying magnetic field, the transducer radiates an ultrasonic beam to scan tissues in the blood vessel normal to the planar surface of the transducer.

FIG. 8 is an exploded view showing how the microactuator is located relative to the transducer. The microactuator 120X can be considered to include the stage 132 having the plate 138 (see FIG. 7) and torsion arms 140A, 140C, as well as the magnetic material 142 layered on the plate. The transducer assembly 124 is moved by the pivotal movement of the plate 138 about the torsion arms 140A, 140C caused by variations of a magnetic field in which the magnetic material is situated. An electromagnet 154 is proximate to the stage 132 to provide the varying magnetic field. The electromagnet 154 contains a coil 156 that is wrapped around a magnet core 152. An electrical current can be passed through the coil 156 to produce a varying magnetic field. The magnet core 152 of the electromagnet 154 extends parallel to, preferably along, the axis 123 of the ultrasonic probe. This means that a long magnet core can be used to increase the number of turns of the coil, since the length of the electromagnet can extend along the axis 123 and is not limited by the diameter of the ultrasonic probe in this embodiment. Such an actuator is suitable for use in an ultrasonic probe similar to that shown in FIG. 4. The coil 156 is wrapped such that the axis of the coil is perpendicular to the plane of the stage 132 and the plate 138 is located generally at about the axis of the coil, which is parallel to the axis 123 of the ultrasonic probe. In this way, the lines of the magnetic field pass through the plate 138 in a direction generally perpendicular to the plane of the stage 132. The stage 132 can be affixed to the electromagnet 154 by commonly known affixing means, such as adhesive, clips, clamps, and the like. Optionally, a tube 160 with an end plate 162 can be used to anchor and protect the stage 132 and the electromagnet 154. It is noted that if a short magnet core is used such that the electromagnet and the stage 132 can fit transversely inside the imaging head 106, this arrangement of the plate 138 with the electromagnet 154 is also applicable for an ultrasonic probe of FIG. 3A FIG. 9A shows an exploded view of another embodiment of a transducer assembly and a microactuator that is especially suitable for an ultrasonic probe of FIG. 3A. In this embodiment, the stage 132 is generally similar to the stage 132 of FIG. 8. The electromagnet 154Y has a U-shaped magnet core 152Y. The magnet core 152Y has an elongated magnet core body 155A with a first leg 155B and a second leg 155C extending about perpendicularly from its ends. The first leg 155B is more distal than the second leg 155C in the ultrasonic probe. A coil 156Y is wrapped around the magnet core 158Y. The axis of the coil is generally parallel to the axis 123 of the ultrasonic probe so that a long electromagnet can be used. The stage 132 is proximate to and preferably rests on the first leg 155B at the distal end of the ultrasonic probe. In this way, the lines of the magnetic field in the electromagnet 154Y are channeled from the elongated magnet core body 155A and pass out of the first leg 155B through the stage 132. Thus, as the current passing through the coil 156Y varies, the electromagnet's magnetic field varies and pivots the plate on the torsion arms 140AY and 140CY. Again, as in FIG. 8, the electromagnet 154Y can be positioned proximate to or affixed to the stage 132. An alternative to a U-shaped magnet core is a L-shaped magnet core, which still allows the stage 132 to be placed on the leg at the distal end of the magnet core. The electromagnet with a U-shaped magnet core or a L-shaped magnet core can also be used in an ultrasonic probe of FIG. 5.

Figure 9B:
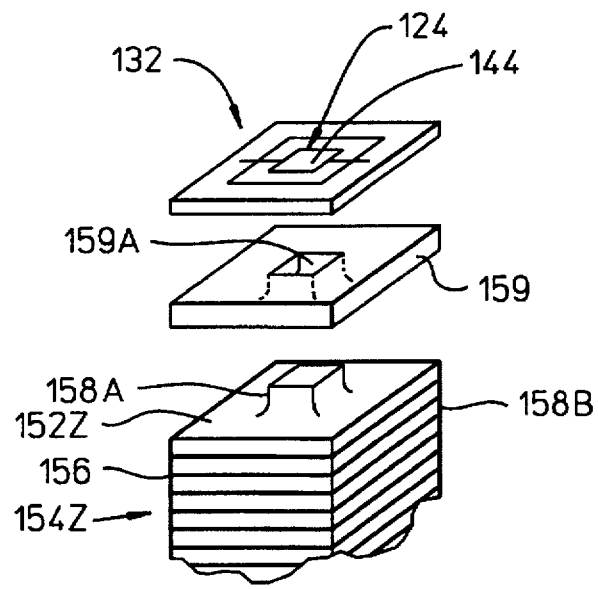
FIG. 9B shows an exploded view in portion of the microactuator of another ultrasonic probe according to the present invention, showing an electromagnet with a core having a finger.

The strength of the electromagnet can be increased by increasing the number of loops in the coil, increasing the cross sectional area of the magnet core (and therefore the size of the loops), and increasing the current in the coil. Since the plate 138 (see FIG. 7) is small and only magnetic field lines passing through the magnetic material on the plate affect the pivotal motion, as shown in FIG. 9B in portion, to increase the effective magnetic field strength, the electromagnet 154Z can have a magnet core 152Z including a finger 158A extending from a larger body 158B. The larger body 158B of the magnet core allows the coil 156 to have larger loops. At the finger 158A, the magnetic field lines are concentrated to pass through the magnetic material on the plate 138. Preferably, a spacer 159 having a void 159A for receiving the finger 158A can be disposed between the larger body 158B of the magnet core and the stage 132 to help secure the stage to the electromagnet 154Z. The spacer 159 can have planar dimensions generally similar to those of the stage 132.

With the above-described arrangements, the stage 132 and the electromagnet can be enclosed in the imaging head 106 without enlarging the radial dimension of the imaging head. Methods of making coils and electromagnets for microactuators are known in the art. Some methods involve using a metallic coil, e.g., by deposition, and some involve doping a silicon material to form the conductive coil for the electromagnet. See, e.g., Wagner et at., "Microactuators with Moving Magnets for Linear, Torsional or Multiaxial Motion," *Sensors and Actuators*, A. 32, 1992, pp. 598–603; Kamins, et al., "Diffusion of Impurities in Polysilicon," *J. Appl. Phys.*, 43 (1), January 1972, p. 83–91; Mandurah, et al., "A Model for Conduction in Polycrystalline Silicon, Part 1: Theory," *IEEE Trans. of Electron. Devices*, Vol. ED-28, No. 10, October 1981, p. 1163–1170; whose descriptions of the methods for doping and for fabricating a microactuator are incorporated by reference herein.

In another embodiment, more than one transducer can be present in the imaging head 106. In fact, more than one stage, each positioned such that the transducer thereon directs an ultrasonic beam at a different direction, can be present. This can be done, for example, by combining the transducer assemblies of FIG. 3A and FIG. 4.

Operation of the Ultrasonic probe

An ultrasonic probe of the present invention can be inserted into a selected body cavity with standard methods known in the art. When an ultrasonic probe of FIG. 6 is in operation, the controller 114 (see FIG. 1) controls the current flow in the coil in the electromagnet. This causes the electromagnet (not shown in FIG. 6) to vary its magnetic field to attract or repel the magnetic material layer 178, which is ferromagnetic.

Figure 10:
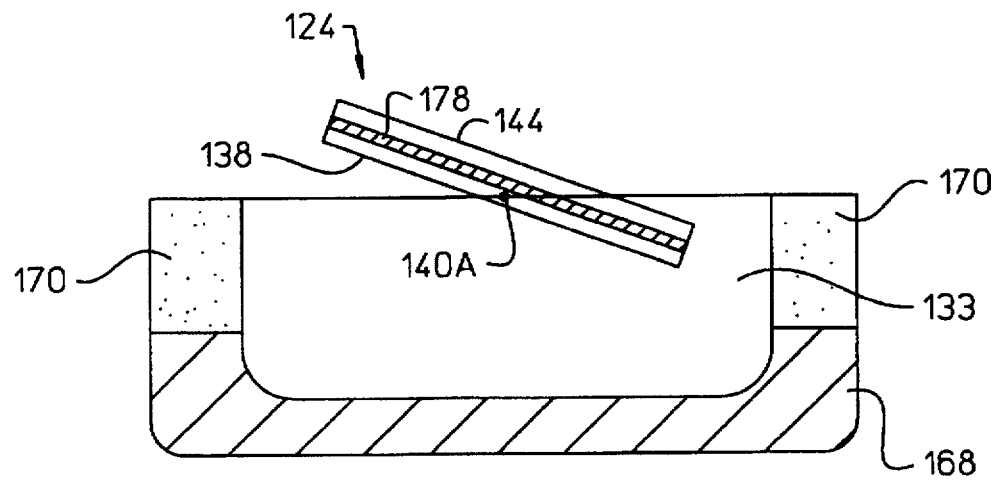
FIG. 10 shows a sectional view of an embodiment of a stage in the ultrasonic probe according to the present invention, showing the transducer being pivoted to face a first direction.
Figure 11:
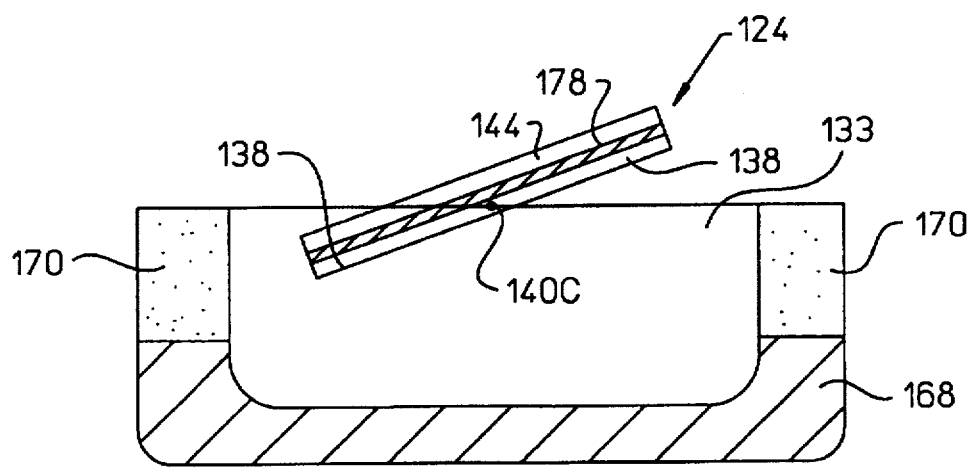
FIG. 11 shows a sectional view of an embodiment of a stage in the ultrasonic probe according to the present invention, showing the transducer being pivoted to face a second direction.
Figure 17A:
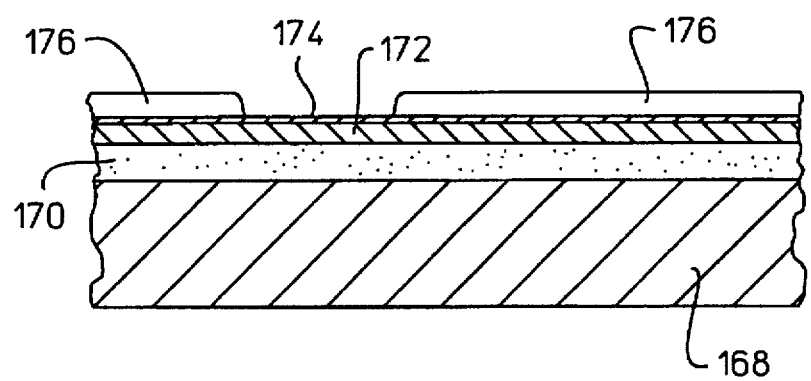
FIG. 17A shows a sectional view of layers of material during the formation of an embodiment of a stage in the fabrication of the microactuator of an ultrasonic probe according to the present invention, showing the preparation for patterning a layer of magnetic material.
Figure 17B:
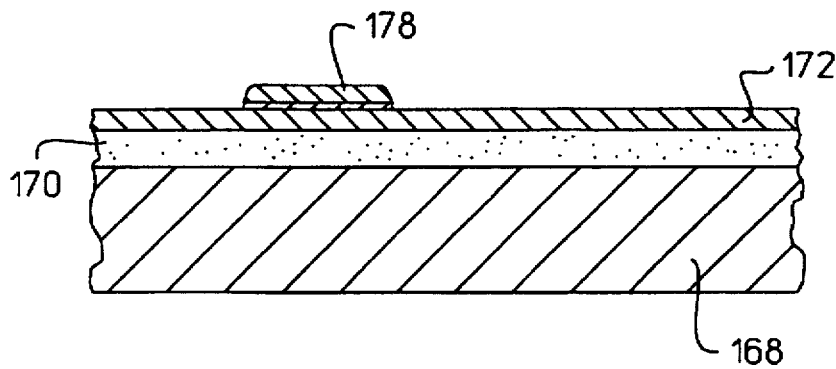
FIG. 17B shows a sectional view of layers of material during the formation of an embodiment of a stage in the fabrication of the microactuator of an ultrasonic probe according to the present invention, showing a layer of magnetic material formed.

FIG. 10 is a sectional view of the stage 132, with an orientation that is the same as that of FIG. 17B (described below), showing the plate 138 being pivoted such that the plane of the plate forms an angle with the plane of the stage. This position can be achieved, for example, by passing an electrical current through the coil of the electromagnet to energize the electromagnet, thereby repelling one half and attracting the other half of the magnetic material layer 178. When the transducer element, e.g., piezoelectric element, in the transducer 144 is electrically excited, ultrasonic pulses are transmitted normal to the plane of the transducer, i.e., generally normal to the plane of the plate 138. As shown in FIG. 11, when an electric current is passed through the coil of the electromagnet in the opposite direction, the respective halves of the magnetic material layer 178 are attracted and repelled by the electromagnet to pivot the plate 138 to a different angle relative to the plane of the stage 132. As the plate 138 pivots, the transducer assembly 124 rocks on the torsion arms such that the ends of the transducer assembly swing back and forth. By repetitively cycling the pivotal motion of the plate 138, the transducer assembly 124 is swept through an angular range to scan tissues encircling the ultrasonic probe.

A way to bias the plate 138 such that the transducer assembly 124 can be at a desired position when no current passes through the coil of the electromagnet is to include a permanent magnet (not shown in the figures), for example, proximate to the magnetic material layer 178. The size and strength of the permanent magnet is selected such that the constant magnetic field of the permanent magnet exerts a continuous force to bias the plate 138 to a desired position. To scan a large area, the ultrasonic probe may need to be moved periodically so as to move the imaging head (labeled as 106 in FIG. 1) to different locations or orientations. This can be done, for example, by advancing or retracting the imaging head along the longitudinal axis of the ultrasonic probe and by turning the probe on the longitudinal axis.

Figure 12:
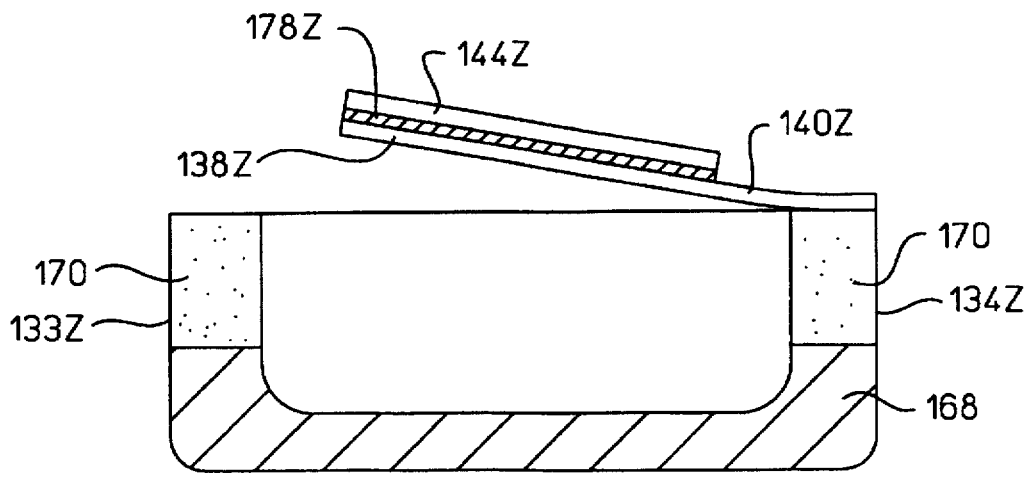
FIG. 12 shows a sectional view of another embodiment of a stage in the ultrasonic probe according to the present invention, showing a flap that is supported at the flap's end.

An alternative embodiment of the ultrasonic probe of the present invention, shown in FIG. 12, includes a flap 138Z linked and supported at one end by support arm(s) 140Z to a wall 134Z surrounding a cavity 133Z. This flap 138Z functions similarly to the plate 138 of FIG. 11 and supports a magnetic material layer 178Z and a transducer 144Z. Such a device can be made, for example, with the method described in Liu, et al. (1995), supra or the method described by Judy and Muller (1995), supra for making microactuators with supporting beams or cantilevers. Again, a permanent magnet can be used to bias the transducer assembly to a desired location when the electromagnet is not activated.

A transducer, e.g., transducer 144, can be used to both transmit and receive ultrasonic signals. As previously stated, the controller 114 is used to control the emission of ultrasonic signals and analyze ultrasonic signals received. Systems for controlling, emission, reception, and analysis of ultrasonic signals are known in the art.

Method of Making the Apparatus

The apparatus with a pivoting transducer can be made by first fabricating an actuator assembly and a transducer block separately and assembling them together. This can be done by adopting micromachining methods for semiconductors known in the art, e.g., Judy and Muller, "Magnetic Microactuation of Torsional Polysilicon structures," *Dig. Int. Conf. Solid-State Sensors and Actuators*, Stockholm, Sweden, Jun. 25–29, 1995, pp. 332–339; Ahn and Allen, "A Fully Integrated Micromagnetic Actuator with a Multilevel Meander Magnetic Core," *Tech. Dig. IEEE Solid-State Sensor and Actuator Workshop*, (Hilton Head '92), Hilton Head Island, S.C., Jun. 22–25, 1992, pp. 14–18; Liu et al., "Out-of-Plane Permalloy Magnetic Actuators for Delta-Wing Control," *Proc. IEEE Micro Electro Mechanical Systems (MEMS '95)*, Amsterdam, The Netherlands, Jan. 29–Feb. 2, 1995, pp. 7–12; Judy and Muller, "Magnetic Microactuation of Polysilicon Flexure Structures," *J. Microelectromechanical Systems*, 4(4), December 1995, pp. 162–169; and Pister et al. "Microfabricated Hinges," *Sensors and Actuators*, A. 33, 1992, pp. 249–256, of which the description on methods of making microactuators are incorporated by reference herein.

Etching methods for various materials used in solid-state semiconductor technology are known in the art. For example, methods for etching silicon dioxide are described in Steinbruchel et al., "Mechanism of dry etching of silicon dioxide—A case study of direct reactive ion etching," *J. Electrochem. Soc. Solid-state and Technology*, 132(1), pp. 180–186, January 1985; and Tenney et al., "Etch Rates of Doped Oxide in Solutions of Buffered HF," *J. Electrochem. Soc. Solid State and Technology*, 120 (8), pp. 1091–1095, August 1973. Polysilicon etching is described by Bergeron et al., "Controlled Anisotropic Etching of Polysilicon," *Solid State Technologies*, August 1982, pp. 98–103; and B. L. Sopori, "A New Defect Etch for Polycrystalline Silicon," *J. Electrochem. Soc. Solid State and Technology*, 131 (3), pp. 667–672, March 1984. Silicon nitride etching is described by van Gelder et al., "The etching of Silicon Nitride in Phosphoric Acid with Silicon Dioxide as a mask", *J. Electrochem. Soc. Solid State and Technology*, 114 (8), August 1967, pp. 869–872. Silicon etching is described by M. J. Declercq, "A New CMOS Technology Using Anisotropic Etching of Silicon," *IEEE J. of Solid State Circuits*, Vol. SC-10, No. 4, August 1975, pp. 191–196; K. E. Bean, "Anisotropic Etching of Silicon," *IEEE Trans. Electron. Devices*, Vol. ED-25, No. 10, October 1978, pp. 1185–1193; Osamu Tabata, "pH-controlled TMAH etchants for silicon micromachining," *Sensors and Actuators*, A53, 1996, pp. 335–339, and Robbins, et al., "Chemical Etching of Silicon II. The system of HF, HNO$_3$, H$_2$O, and HC$_2$H$_3$OO$_2$," *J. Of The Electrochemical Society*, 107 (2), February 1960, pp. 108–111. These etching methods are incorporated by reference herein.

For illustration, an embodiment that includes a silicon substrate layer, a SiO$_2$ sacrificial layer, a silicon nitride layer with two support torsion arms, and a magnetic material layer of NiFe is described below. As is known and the publications above indicate, glass and SiO$_2$ can be etched with suitable chemicals, e.g., buffered hydrofluoric acid (HF) mixtures; silicon can be etched with potassium hydroxide (KOH), preferably with tetramethyl ammonium hydroxide (TMAH); glass, SiO$_2$, polysilicon, and silicon nitride can be dry-etched with plasma chemistry known to one skilled in the art; and silicon nitride can also be wet-etched with phosphoric acid (H$_3$PO$_4$). It is also known that these etching methods affect each material (e.g., silicon, silicon nitride, polysilicon, SiO$_2$, NiFe) differently. This difference is due to the materials' inherent physical and chemical properties. The different etch rates for such materials using a wide variety of etchants will allow the ability to etch differentially one material quickly and another very slowly. On the support (i.e., silicon nitride, polysilicon) layer is deposited the magnetic material, e.g., nickel ferrite (herein referred to as NiFe) permalloy consisting of 80% nickel and 20% iron. In scientific literature, this material with 80% nickel and 20% iron is sometimes represented by Ni$_{80}$Fe$_{20}$. It is noted that other magnetic materials can also be used, as long as it can be attracted by the electromagnet to pivot the plate.

An alternative to polysilicon or silicon nitride is polyimide, e.g., PI-2611 from DuPont Company (Wilmington, Del.). A polyimide layer is typically formed by spinning. Such a layer can be etched by dry plasma etching. Polyimide materials suitable for such applications are available commercially from chemical suppliers such as DuPont Company and Ciba Geigy Corp. (Greensboro, N.C.). Methods of spinning and etching a polyimide layer are known in the art. See, e.g., Ahn, et al., "A Planar Variable Reluctance Magnetic Micromotor with Fully Integrated Stator And Wrapped Coils," *Proc. IEEE Micro Electro Mechanical Systems (MEMS '93)*, Fort Lauderdale, Fla., February 7–10, 1993. A layer of such materials, e.g., silicon nitride, polysilicon, polyimide, that can be used to form the support arms is herein referred to as "transducer-support layer" since the support arms and the bottom layer of the transducer assembly are formed from such layers.

Figure 13:
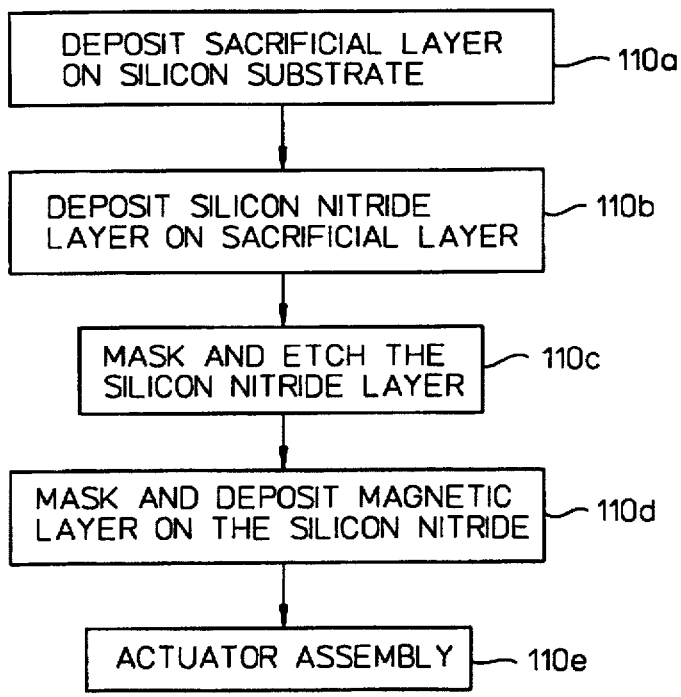
FIG. 13 shows a flow diagram for forming an actuator assembly of the present invention.
Figure 15:
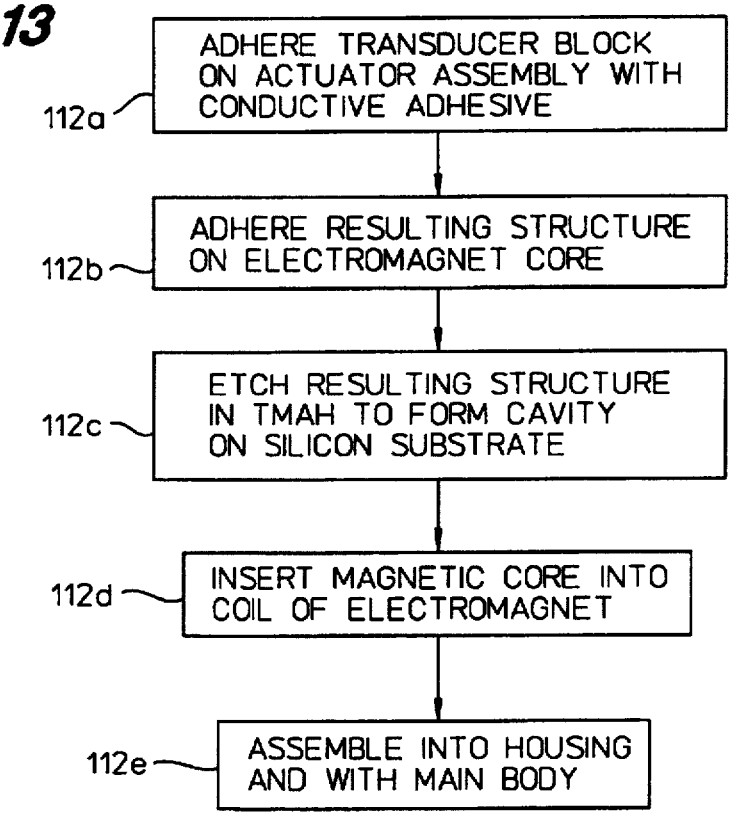
FIG. 15 shows a flow diagram for forming an ultrasonic probe with the actuator assembly and transducer block according to the present invention.
Figure 14:
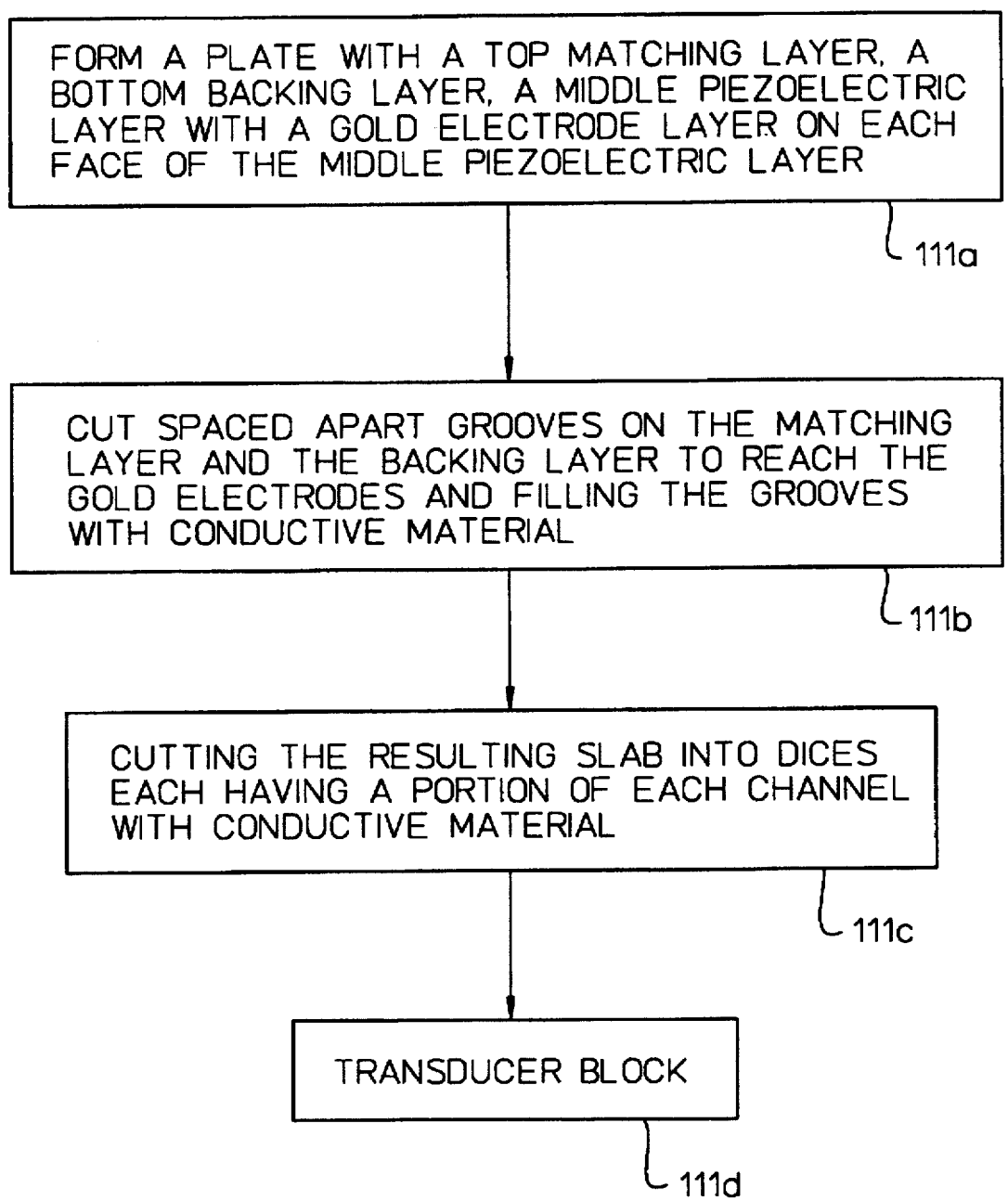
FIG. 14 shows a flow diagram for forming a transducer block of the present invention.

FIGS. 13 to 15 show the flow diagram of a preferred process for making an ultrasonic probe according to the present invention. An actuator assembly and a transducer block are made separately. The two are assembled on a steel core of an electromagnet and then the resulting structure is immersed in TMAH to etch the cavity on the silicon substrate. As shown in FIG. 13, the actuator assembly is made by first depositing a sacrificial layer (e.g., silicon dioxide) on silicon substrate (step 110a). A transducer-support layer of silicon nitride is then deposited on the sacrificial layer (step 110b). The silicon nitride on this structure is then masked and etched to form the desired design, with support arms, support platform for the magnetic material, etc. (step 110c). A layer of magnetic material (e.g., NiFe) with the desired design is then deposited on the transducer-support layer by masking and deposition (e.g., by sputtering and electroplating) (step 110d). This forms the actuator assembly (step 110e). The silicon substrate is not etched yet.

As shown by FIG. 14, the transducer block 180 is made by first forming a block with a top acoustic matching layer, a middle piezoelectric layer, a bottom backing layer, with a gold electrode layer interposed between the matching layer and the piezoelectric layer and between the backing layer and the piezoelectric layer (step 111a). Although called a transducer "block," the resultant structure is actually thin and shaped more like a plate. On this plate-shaped structure, spaced-apart grooves (or channels or void areas) are cut on the matching layer and the backing layer to penetrate them, reaching the piezoelectric layer, or at least the gold electrode layers. The grooves are filled with electrically conducting material, e.g., silver epoxy and annealed, or cured (step 111b). The resulting plate is cut into blocks (or dices), each have a portion of the conducting material (step 111c). The resulting dices are coated with an electrically and moisture insulating coating on the side surfaces to prevent unintended electrical connections. The coating may be disrupted in a selected area on each block to expose the conductive material for electrical connection. This forms the transducer blocks (step 111d).

As shown in FIG. 15, a transducer block is then attached on top of an actuator assembly with conductive adhesive (e.g., silver epoxy) (step 112a). This is then affixed onto the electromagnet core with conductive adhesive (step 112b). The resulting structure is then immersed in TMAH to etch the cavity 133 on the silicon substrate (step 112c). The magnetic core is then inserted into the coil of the electromagnet (step 112d). The resulting structure is assembled with the housing, main body, and the like, to form the ultrasonic probe (step 112e).

Forming the actuator assembly

Figure 16:
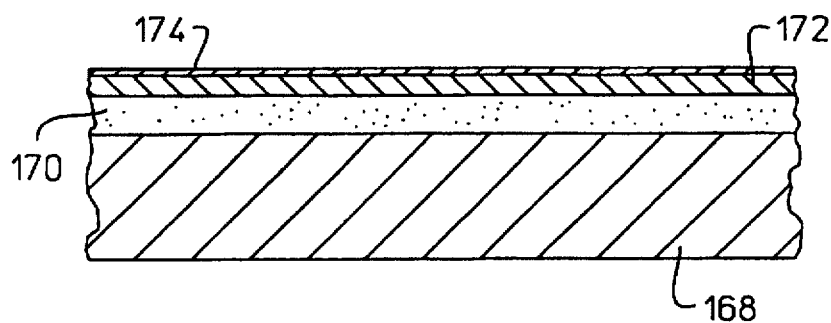
FIG. 16 shows a sectional view of layers of material during the formation of an embodiment of a stage in the fabrication of the microactuator of an ultrasonic probe according to the present invention.

As an illustrative example, as shown in FIG. 16, a $SiO_2$ sacrificial layer 170 of a desired shape, size, thickness, and pattern is formed on a silicon substrate 168. The sacrificial layer 170 is covered with a $Si_3N_4$ layer 172. This $Si_3N_4$ layer 172 is then covered with a photoresist, masked, and etched to form the desired size, shape, and pattern suitable to support the magnetic material and the transducer and to withstand the rigor of repeated torsional turning of the torsional arms during operation.

The silicon nitride layer 172 can be lithographically masked and patterned with hot $H_3PO_4$ at about 50° C. The acid will etch completely through the exposed silicon nitride areas relatively quickly but the etch rate will slow down considerably, i.e., in orders of magnitude, on the exposed $SiO_2$ layer 170. The lithographic masking material on top of the silicon nitride layer can be removed by an oxygen plasma with minimal effect on the exposed $SiO_2$ layer 170. Neither will the oxygen plasma affect the exposed silicon nitride layer. At this stage of the process, the lithographic masking material on the silicon nitride has been removed and the opening in the silicon nitride layer exposes a thin layer of $SiO_2$. A brief characterized timed dip, e.g., of about 10 seconds, in a 10:1 hydrofluoric acid will remove the exposed $SiO_2$ layer 170. The silicon substrate 168 is now exposed. If desired, the exposed $SiO_2$ layer 170 can be removed after the magnetic material or the transducer block is put in place.

A conductive seed film 174, e.g., containing a chromium film and a copper film, is then vapor deposited on the selected surface on the $Si_3N_4$ layer 172 to facilitate the deposition of the magnetic material. In FIG. 17A, a layer of photoresist 176 is used to cover areas of the $Si_3N_4$ layer 172 and other surfaces on which deposition of magnetic material is not desired. A NiFe layer 178 of the desired thickness is then electroplated on the portion of the $Si_3N_4$ layer 172, i.e., on the conductive seed film 174, not covered by the photoresist 176. In FIG. 17B, after removal of the photoresist and the conductive seed film 174 in selected areas, a NiFe layer of the desired size, thickness, and shape remains on the $Si_3N_4$ layer 172. This NiFe layer in a preferred embodiment will function both as a magnetic material for driving the pivotal motion in the presence of a magnetic field and as a conductor for activating the transducer to produce ultrasound and for conducting electrical signals from the transducer after receiving ultrasonic signals. As shown in FIG. 23 below, on the two sides of the stage 132, the NiFe forms connection pads 148A, 148C for connecting to active potential and ground.

Forming the transducer block

Figure 18A:
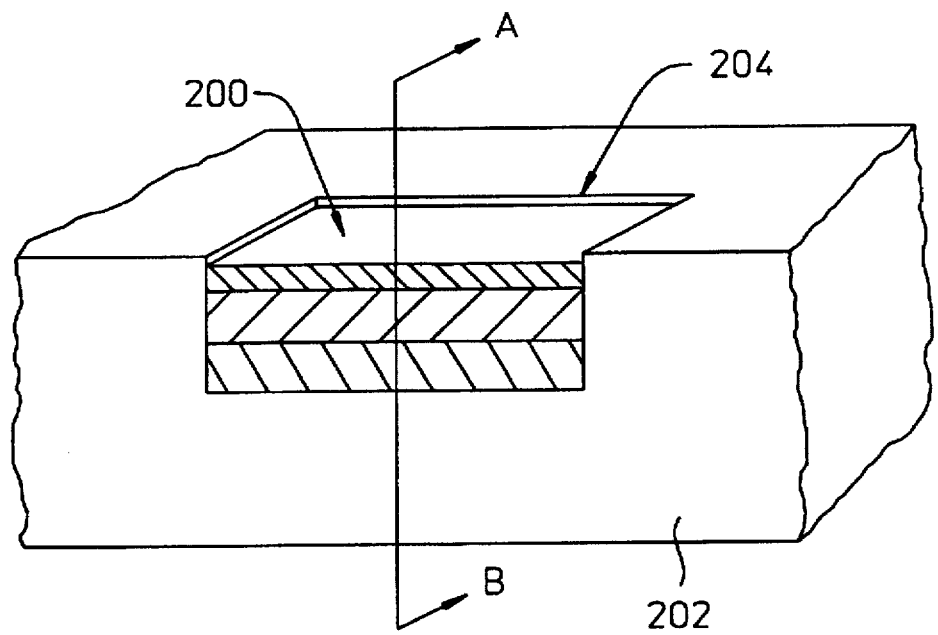
FIG. 18A shows an isometric view of a dressing block with a plate of backing layer, transducer layer, and matching layer according to the present invention.
Figure 18B:
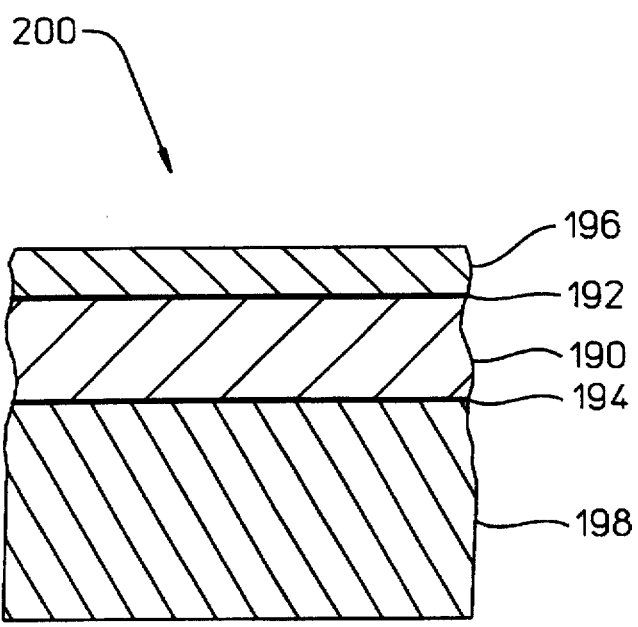
FIG. 18B shows an sectional view of the plate of FIG. 18A cut along line A–B.

An illustrative embodiment for forming the transducer block is described in the following. As previously stated, to form a transducer block, a plate-shaped structure with matching layer, piezoelectric layer, gold electrodes and a backing layer is made first. This is shown in FIGS. 18A and 18B. FIG. 18B is the sectional view along line A–B in FIG. 18A. In the plate 200, the piezoelectric layer 190 is sandwiched between a top electrode 192 and bottom electrode 194 (preferably made of gold) on its top and bottom surface, respectively, and having a top matching layer 196 and a bottom backing layer 198.

First, a thicker piezoelectric (PZT) plate is lapped (i.e., polished) to a desired, uniform thickness. Gold 192 is then deposited on one face of the PZT layer 190. A thicker matching layer 196 is lapped to a desired, uniform thickness and adhered to the gold 192 on the PZT layer by adhesive and annealed to set the adhesive. The PZT layer 190 in the resulting structure is lapped again to achieve a desired thickness. Gold 194 is deposited on the PZT layer 190 on the exposed PZT surface (remote from the matching layer). A backing layer 198 is lapped to a desired, uniform thickness. This is adhered to the exposed gold on the PZT and annealed. The matching layer 196 is lapped to a desired uniform thickness. This forms the plate 200. The plate 200 is placed on a dressing block 202 with a cut-out 204 which fits the plate snugly. This dressing block 202 will facilitate cutting of grooves, filling of cuts, block-cutting, and handling of the plate 200.

Figure 19A:
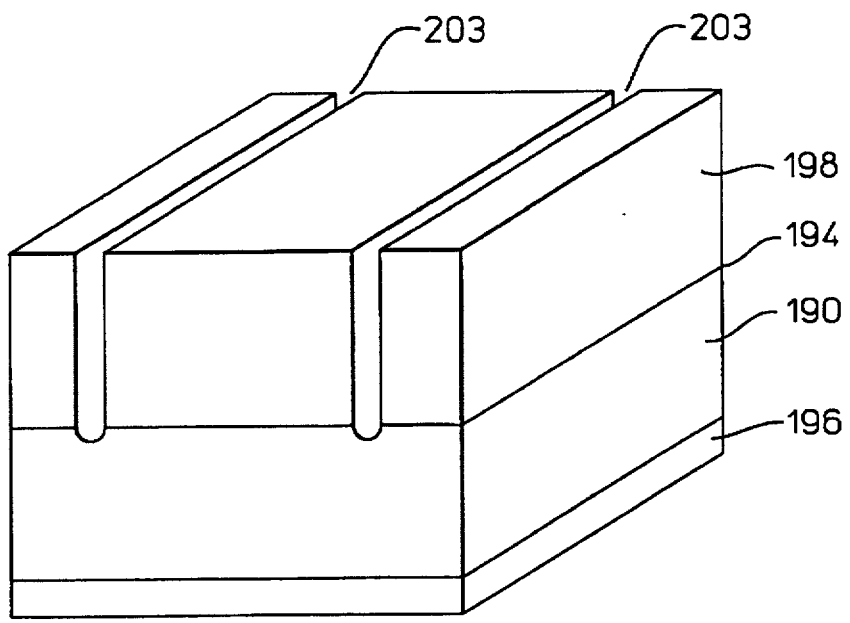
FIG. 19A shows an isometric view of a portion of the plate of FIGS. 18A–18B with grooves cut in the backing layer according to the present invention.
Figure 19B:
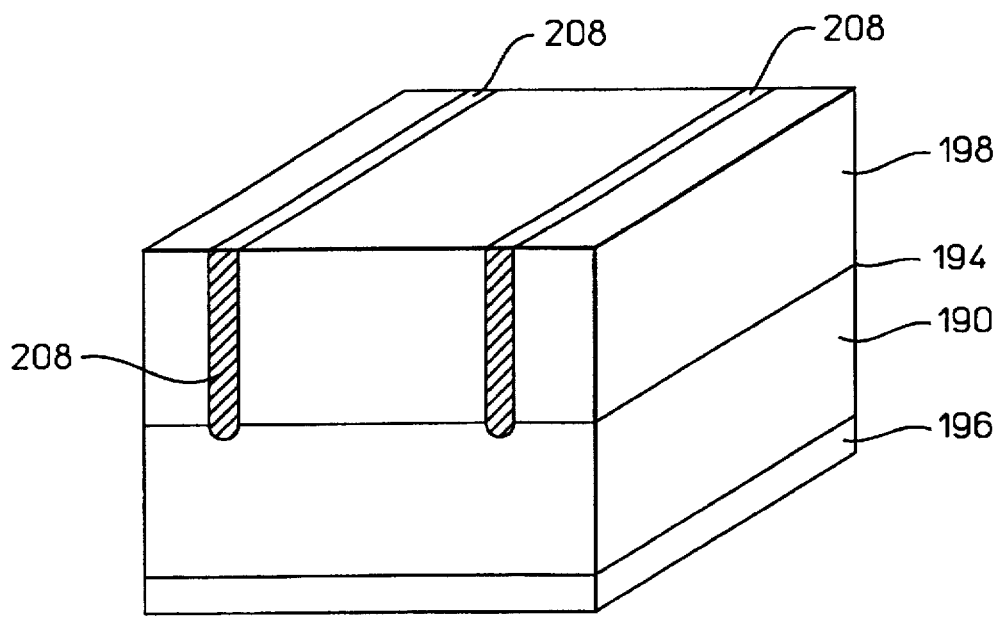
FIG. 19B shows an isometric view of the portion of the plate of FIGS. 18A–18B with the grooves filled with conductive materials in the backing layer according to the present invention.
Figure 20A:
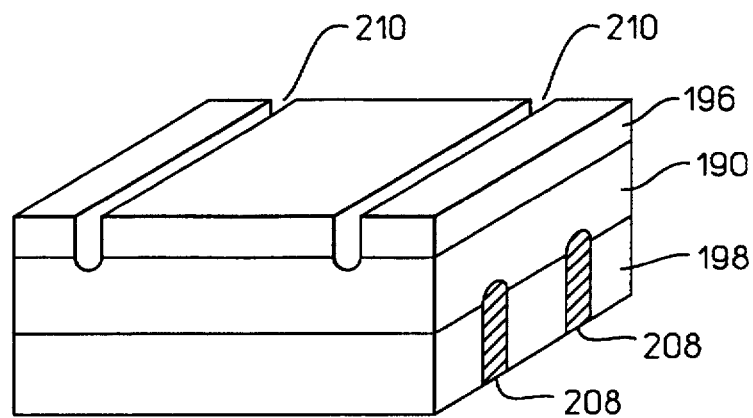
FIG. 20A shows an isometric view of the portion of the plate of FIGS. 18A–19B with grooves cut in the matching layer according to the present invention.
Figure 20B:
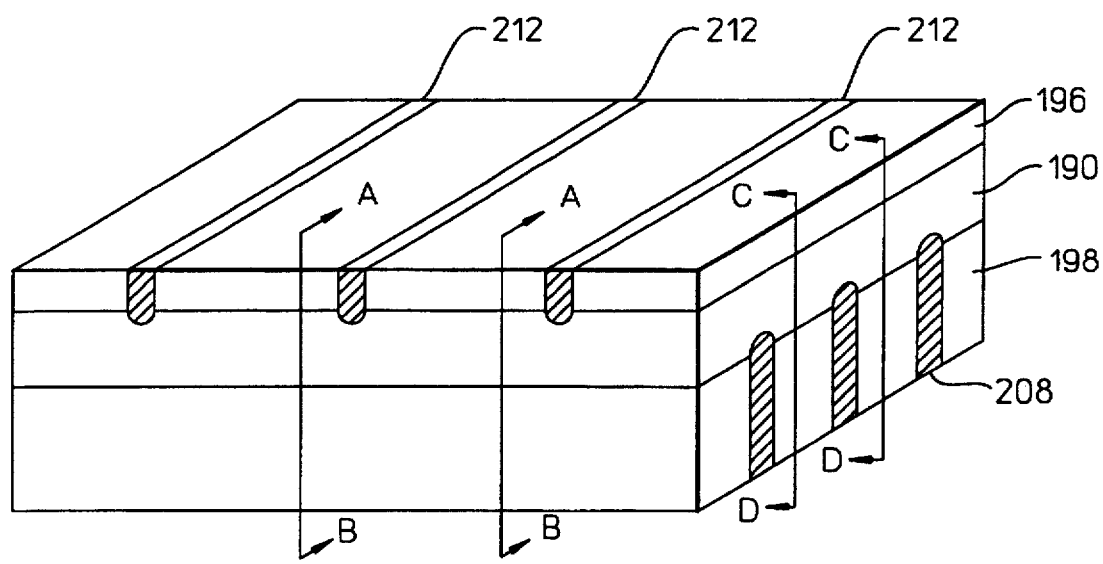
FIG. 20B shows an isometric view of a portion of the plate of FIGS. 18A–20A with the grooves filled with conductive materials according to the present invention.

On the dressing block 202, the plate 200 is cut to form an array of preferably parallel, straight grooves 203 on the backing layer 198 such that the grooves penetrate to the piezoelectric layer 190, or at least to the bottom electrode 194 (FIG. 19A). The grooves 203 are cleaned and then filled with a conductive material, e.g., silver epoxy, which will be cured to solidify to become bottom conductors 208 (FIG. 19B). The matching layer is cleaned to ensure uniform thickness. Another array of preferably parallel, straight grooves 210 are cut on the matching layer 196 such that they (i.e., top grooves) penetrate to the piezoelectric layer 190, or at least to the top electrode 192 (FIG. 20A). Preferably, these top grooves 210 are perpendicular to the bottom grooves 203 to facilitate block-cutting later, although parallel arrangement can also be used if grooves 203 and 210 are spaced apart adequately. The top grooves 210 are filled with conductive material (e.g., silver epoxy) and cured to form top conductors 212 (FIG. 20B). If preferred, the top and bottom grooves can be cured separately. Also, the matching layer can be cut and filled before the backing layer.

Figure 21:
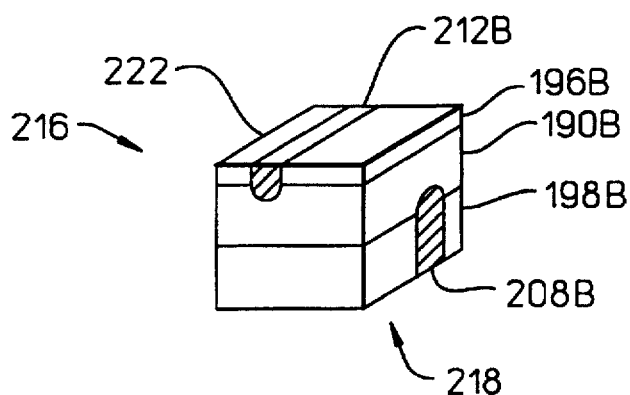
FIG. 21 shows an isometric view of a transducer block made by cutting the plate of FIG. 20B along plane A–B and C–D.

Edges on the resulting plate 200 are trimmed to ensure that the conductors are exposed for electrical connection. The plate 200 is then tested to ensure that they are adequately poled. Then the plate 200 can be cut into dices (or transducer blocks) 216, see FIG. 21, such that each block has a portion of a bottom conductor 208B and a top conductor 212B. It is noted that the blocks are not cubes but are rather thin and flat. As shown in FIG. 20, the cut planes A–B and C–D are perpendicular and evenly spaced between the top and bottom conductors.

Each of the blocks 216 formed is then cleaned and coated with an electrically and moisture-insulating coating (not shown for clarity), e.g., a polymeric coating, such as PARYLENE (Specialty Coating Systems, Inc., Indianapolis, Ind., U.S.A.) on the side surfaces. Then, on each block 216, the coating on a bottom edge 218 with a bottom conductor 208B and a top edge 222 with a top conductor 212B are disrupted to expose the conductors at these edges, e.g., by rubbing these edges on an abrasive surface, e.g., fine sandpaper, steel surface, graphite bar, and the like. In each block, the top conductor 212B and bottom conductor 208B are considered to "penetrate" the matching layer and the backing layer respectively because they extend through the entire thickness of the respective layers.

Figure 22:
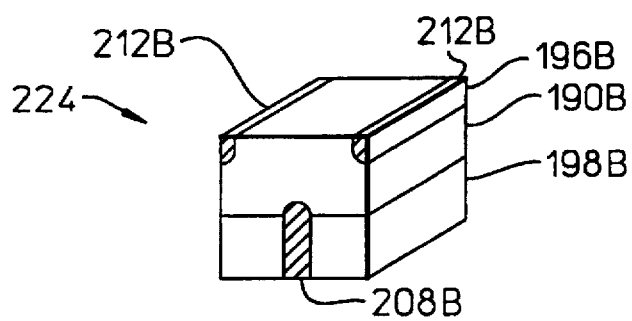
FIG. 22 shows an isometric view of an alternative transducer block according to the present invention.

An alternative transducer block 224 (see FIG. 22) with the top conductor 212B and bottom conductor 208B running in parallel can be formed if the grooves 210 and 212 are cut in parallel as previously described. Furthermore, depending on where and how the cutting is done, other alternative designs of transducer blocks can be made with the plates described above. The present technique of making transducer blocks is well suited for mass production.

Forming the stage and the electromagnetic drive

Figure 23A:
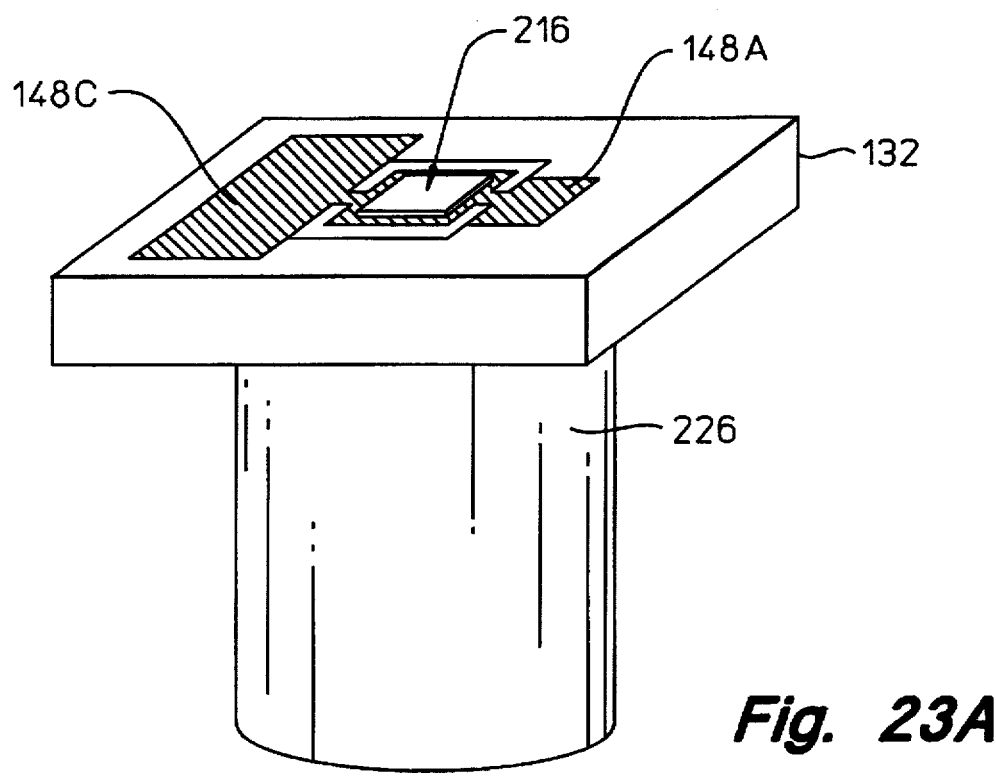
FIG. 23A shows an isometric view of the stage of present invention attached to a core of an electromagnet according to the present invention.
Figure 23B:
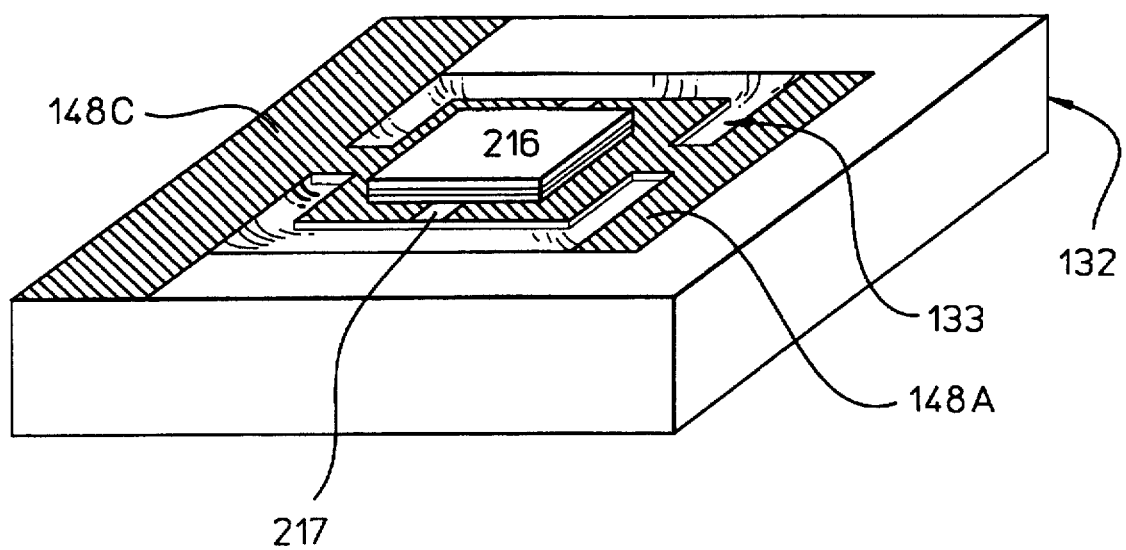
FIG. 23B shows an isometric view of the stage according to the present invention.

As shown in FIGS. 23A and 23B, a transducer block, e.g. block 216 is affixed with adhesive on the magnetic material (NiFe) layer 178 on the $Si_3N_4$ transducer support layer 172. Silver epoxy is used for connecting the appropriate top and bottom conductors 212B and 208B to the NiFe layer for providing electricity to the piezoelectric layer 190B, which lies between matching layer 196B and backing layer 198B. The silver epoxy is applied such that it covers as little of the top of the matching layer as possible and such that the top conductor 212B and bottom conductor 208B are not connected to each other by the silver epoxy. This forms the stage 132 (in which, at this time, the cavity has not been formed yet). It is noted that a gap 217 separates the magnetic material leading to the two torsion arms. This allows the two torsion arms to be used for leading to electrical connections, e.g., connection pads 148A, 148C, of different voltage. The stage 132 is attached to a core 226 of the electromagnet with adhesive.

Figure 24:
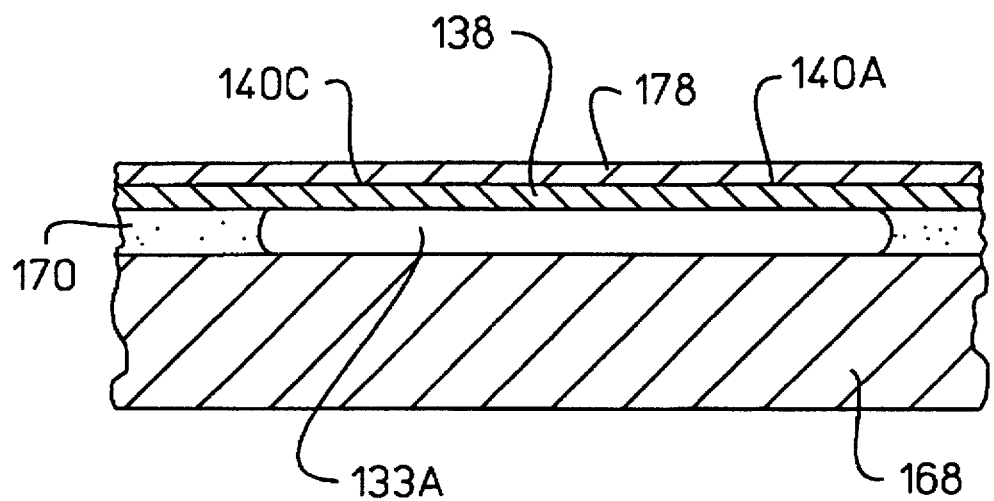
FIG. 24 shows a sectional view of the stage being etched according to the present invention.
Figure 25:
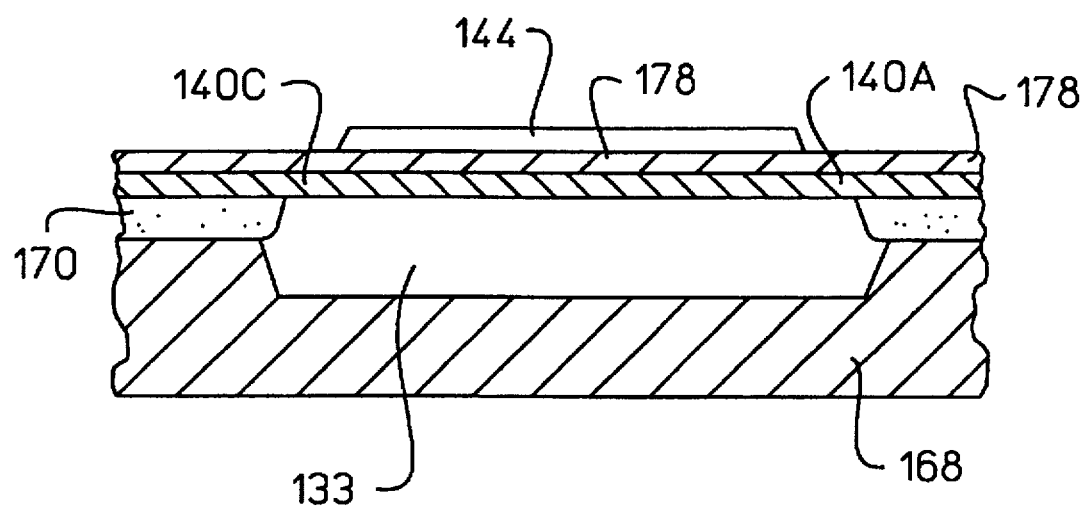
FIG. 25 shows a sectional view of the stage having a cavity etched according to the present invention, showing a transducer disposed on the plate.

The stage 132 with the core 226 is then etched to form the cavity 133. In the sectional view shown in FIG. 24, to shape the substrate 168 defining the cavity 133 (see, cavity 133 in FIG. 6), the sacrificial layer 170 beneath the portion of the $Si_3N_4$ layer 172 which is designated to be the plate 138 and the torsion arms, if not already etched, is etched by HF. After etching away the selected material of the sacrificial layer 170 to form a small void 133A, the desired silicon substrate area is exposed (compare with FIGS. 14B and 15, which have an orientation perpendicular to FIG. 24 and FIG. 25). This exposed silicon substrate area in the silicon substrate 168 will be immersed in a TMAH solution for an appropriate period of time to etch the cavity 133 (FIG. 25). Depending on the size and shape of the transducer block, torsion arms, and the stage, this period can be readily predetermined with routine testing. Generally, this can be done with TMAH solution at about 85° F. (29.5° C.) at a rate of about 25 μ/hr. We have found that TMAH in the range of about 15 wt % to 25 wt % concentration, temperature of about 80° F. (26.5° C.) to 85° F. (29.5° C.), will minimally affect the $SiO_2$ layer 170, the silicon nitride layer 172 and the PZT piezoelectric layer. This is more advantageous than using KOH solution which tends to attack the PZT lead zirconium titanate piezoelectric material. After etching, the stage is then rinsed clean, e.g., with deionized water. After drying, this stage-core assembly is inserted into the coil 228 of the electromagnet 154.

Figure 26:
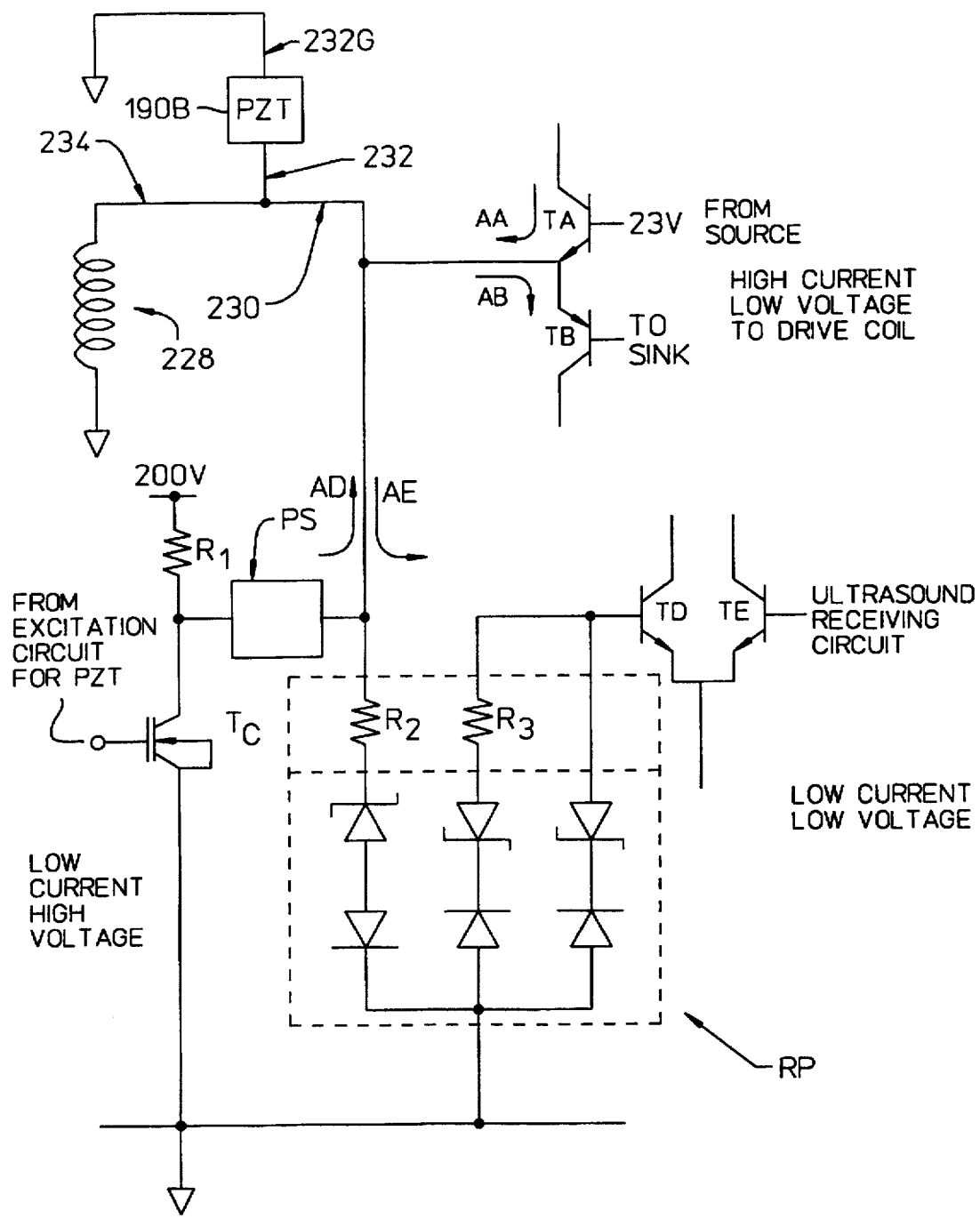
FIG. 26 shows a schematic representation of the circuitry for driving the transducer and the microactuator.

Subsequently, other connections and parts of the ultrasonic probe are made to provide mechanical and electrical connections for the apparatus to function. For example, conductor pad (NiFe) 148A can be connected to the active potential and conductor pad 148C can be connected to ground. In a preferred embodiment, both the transducer and the electromagnet 154 are powered with a single active, i.e., hot, electrical conductor (e.g., the core of coaxial cable 128). Since the transducer is driven by a relatively high voltage and low current and the electromagnet is driven by a relatively low voltage and high current, a single conductor can be switched between a circuit that produces the relatively low voltage, high current supply and a circuit that provides the relatively high voltage, low current supply. An embodiment of the circuit for the mechanism is shown in FIG. 26. Here, the core 230 of the coaxial cable 128 is connected to conductor 232 on a torsion arm and to conductor 234 leading to the excitation end of coil 228 of the electromagnet. Another conductor 232G on another torsion arm leads from the transducer PZT layer 190B to ground.

The circuit in FIG. 26 operates as follows. The transistor TA drives the electromagnetic coil 228 via the conductors 234 and 230. Since voltage on the conductors from the transistor TA is low, less than the necessary voltage to activate the transducer PZT layer 190B, only the electromagnetic coil will respond. Transistor TB will act in a similar way as TA, except for the current direction presented on the conductors 230 and 234. This is typical push-pull arrangement known to one skilled in the art of circuit design. The arrows AA and AB depict the direction of the current flow in the push-pull circuit, which will result in a change in the electromagnetic field poles of electromagnetic coil 228.

When transistors TA and TB are in the quiescent state, Transistor TC would be used to drive a high voltage but low current pulse onto the conductors 230 and 234 at the appropriate time. The pulse shaping network PS is designed to provide the appropriate pulse shaping for the transmit signal to the transducer, which includes PZT layer 190B. This type of pulse shaping circuitry is generally known to those skilled in the art. This low current pulse would not affect the electromagnetic coil 228. It would only allow the PZT transducer layer 190B to transmit an ultrasonic wave.

During the transmission of the pulse signal, the ultrasonic receiving circuitry is not affected. This is due to the current limiting and voltage clamping protection network RP. Such receiver protection network circuitries are known to those skilled in the art. The generated receiving pulse from the PZT layer 190B is both very low voltage and low current which would not affect the electromagnet. However, it would be seen by the differential amplifier front end circuit having transistors TD and TE and sampled at the appropriate time. Arrow AD shows the direction of current in exciting the PZT layer 190B to generate pulses and arrow AE shows the direction of current in receiving signals from the PZT layer. Appropriate gating transistors, filtering inductors, and decoupling capacitors would be used in the circuit shown. Such are known to those skilled in the art.

Depending on the application of the ultrasonic probe, the size, shape, thickness, and other dimensional characteristics of the microactuator and the transducer can vary to adapt to the application. For example, an intravascular ultrasonic probe will have dimensions much smaller than those of an endoscopic ultrasonic probe. For intravascular ultrasonic probes, the substrate 168 generally can have a thickness of about 100 to 700 μm, preferably about 400 to 500 μm. The plate 138 (see FIG. 6) is preferably rectangular and have a thickness of about 2000 to 10,000 Å, preferably about 4,000 to 9,000 Å (not including the transducer block). The plate 138 can have a width of about 0.2 to 0.7 mm, preferably about 0.3 to 0.4 mm, and a length of about 0.2 to 2 mm, preferably about 0.5 to 1 mm to provide an adequate surface to support the transducer. The torsion arms 140A, 140C are preferably relatively short compared to the width of the plate so as to result in less stress due to the weight of the plate. However, the torsion arms 140A, 140C should be sufficiently long to allow the pivotal motion of the plate 138 to sweep over a desired angle, which corresponds to the angle swept by the normal of the plate. This angle is less than 180° and typically about 10° to 90°. It preferably is about ±45° with respect to the normal of the plate.

Additionally, it is preferred that the width of the plate 138 not be excessive such that the plate does not strike the base of the cavity 133. A wider plate would also require a larger force to turn the plate 138 on the torsion arms 140A, 140C and result in a slower sweep cycle. Generally, the plate 138 can vary from a square shape to a rectangular shape with a width (i.e., the side perpendicular to the torsion arms) to length ratio of about 1:3 to 1:1, preferably about 1:2. Preferably, the length is parallel to the torsional arms 140A, 140C to decrease the force needed to pivot the plate.

As previously stated, the magnetic material is preferably deposited on the upper surface of the plate 138 on both sides of the torsion arms 140A, 140C. If the layer of magnetic material, e.g. NiFe layer 178 is formed such that the N pole is on one side and the S pole is on the other side of the torsion arms 140A, 140C on the surface of the plate 138, a pole of the electromagnet (see, e.g., FIG. 8, electromagnet 154)) below the plate, when a magnetic field is applied by the electromagnet to the plate 138, it will exert an attractive force on the magnetic material on one half of the plate and an repulsive force on the magnetic material on the other half. In this way, the plate 138 is turned about the torsion arms. When the electromagnet reverses polarity, it pivots the plate 138 in the opposite way.

Preferably, to use the surface area of the plate efficiently, the magnetic material occupies substantially all of the upper surface of the plate. Its thickness is preferably less than 25% that of the plate, i.e., the $Si_3N_4$ layer. Various modifications of the above electromagnetic actuation can be contemplated. For example, the pole of the electromagnet can be placed under one side of the plate 138. Another way of actuation is to form the magnetic material on the plate 138 such that the one pole (e.g., the N pole) is on top and the opposite pole is on the bottom and place two poles of an electromagnet each under a different half of the plate.

Preferably, the transducer 144 covers substantially all of the upper surface of the magnetic material 178 and that of the plate 138 (which is not covered by the magnetic material), to use the plate's surface efficiently. The transducer 144 can have the usual electrodes, conductors and transducer element, as known in the art for a transducer in ultrasonic probes. As an example, an intravascular ultrasonic probe can have a silicon substrate layer about 500 µm thick. The $Si_3N_4$ plate can be about 9,000 Å thick, 400 µm wide, and about 1,000 µm long. The NiFe layer 178 can be about 10 µm thick and covers essentially all of the upper surface of the plate. The transducer can be made of a layer of piezoelectric material (e.g., PZT lead zirconium titanate) of about 80 µm thick, a quarter-wave matching layer of graphite about 40 µm thick, and a thick backing material of epoxy and tungsten about 300 µm thick. It can cover essentially all of the upper surface of the plate, therefore covering the NiFe as well. The transducer may also be of quarter-wave material with an appropriate matching layer material such as graphite. Both acoustic matching and backing techniques for making transducers, as well the applicable materials, are known in the art.

The combined thickness of the transducer, the magnetic material, the sacrificial layer, and the plate is thin compared to the length and width thereof. Thus, the combined structure is still generally plate-shaped. The torsion arms 140A, 140C can each be about 5 to 20 µm long. The substrate 168 can have a thickness of about 400 to 500 µm. This will accommodate a cavity 133 of about 300 to 400 µm deep. The sacrificial layer 170 is very thin, generally about 150 to 500 Å. Therefore, the stage 132 has about the same thickness as the substrate 168.

As previously stated, the actuating mechanism and the stage 132 with the transducer assembly are located in the housing 122, which is substantially transparent to ultrasound. The housing is preferably constructed to be mechanical sturdy and has a proper thickness to withstand being manipulated in the insertion process. The ultrasonic probes of the present invention has the usual structures that allows the proper function of typical ultrasonic probes. For example, an imaging guidewire can have a low-friction surface on the main body suitable for a sheath to slide on and be guided to a desire location. Commonly known techniques can be used for making such structures.

Although the illustrative embodiments of the ultrasonic probe of the present invention and the method of using and making the probe have been described in detail, it is to be understood that the above-described embodiments can be modified by one skilled in the art, especially in sizes and shapes and combination of various described features without departing from the scope of the invention.

What is claimed is:

1. Ultrasonic probe for imaging tissues from inside a patient's body cavity having a wall, the ultrasonic probe having a distal end suitable for inserting inside the body cavity and a proximal end opposite the distal end, comprising:

(a) elongated main body portion;
   (b) end portion connected distally to the elongated main body portion, comprising:
      (i) support means having silicon substrate;
      (ii) back and forth pivotable transducer assembly for transmitting an ultrasonic beam, the transducer assembly being supported by the support means and including a base layer connected to the support means via one or more twistable or flexible support arms, a layer of ferromagnetic material above said base layer, and a transducer block with generally flat faces and straight edges on said ferromagnetic layer, said transducer block including a backing layer, a transducer layer on said backing layer, an acoustic matching layer on said transducer layer, a bottom electrode to connect electrically a bottom face of the transducer layer to a conductor which is on a first face of the block, a top electrode to connect electrically a top face of the transducer layer to a conductor on a second face of the block for activating the transducer layer, each of said conductors on said faces of the block being electrically connected for excitation of the transducer layer, said support arms allowing the pivotal motion of the transducer assembly to scan the ultrasonic beam at the wall of the body cavity for imaging: at least one of said bottom electrode and top electrode penetrating the backing layer or the acoustic matching layer; and
      (iii) driver in said end portion for driving fie pivotal motion of the pivotable transducer assembly, the driver being located proximate to the transducer assembly such that all driving motions occur proximate to the distal end of the ultrasonic probe.

2. The ultrasonic probe according to claim 1 wherein the pivotable transducer assembly is plate-shaped and having two support torsion arms which are twistable to allow pivotal motion of said pivotable member.

3. The ultrasonic probe according to claim 2 wherein the pivotable transducer assembly has two support arms one on each side of said assembly and the bottom electrode is in electrical communication with conductor on one support arm and the top electrode is in electrical communication with conductor on the second support arm.

4. The ultrasonic probe according to claim 2 wherein the pivotable member has a support arm made of a material selected from the group consisting of polysilicon, silicon nitride, and polyimide.

5. The ultrasonic probe according to claim 1 wherein the transducer layer includes a bottom electrode layer and a top electrode layer disposed on each face of the piezoelectric material of the transducer layer and connected to the bottom electrode and the top electrode respectively.

6. The ultrasonic probe according to claim 1 wherein the driver has no rotational mechanism for driving a rotational motion in the ultrasonic beam transmitting means in 360° cycles relative to the support means to scan the ultrasonic beam.

7. The ultrasonic probe according to claim 1 further comprising an electrical circuit and a conductor connected to the driver and to the transducer layer, such that said conductor is capable of driving the back and further pivotal motion of the pivotable transducer assembly when not activating the transducer layer and is capable of activating the transducer layer when not activating the driver.

8. The ultrasonic probe according to claim 7 further comprising a controller for switching to activate the transducer layer with relatively high voltage and low current and to drive the pivotal motion with relatively low voltage and high current such that the same conductor can be used to energize the driver and the transducer layer.

9. The ultrasonic probe according to claim 1 wherein the silicon substrate has a cavity thereon defined between said transducer assembly and the silicon substrate such that the pivotable transducer assembly pivots about the cavity.

10. The ultrasonic probe according to claim 9 wherein the support means has a substrate of silicon and some of the silicon of said substrate has been selectively removed by chemical etching with tetramethyl ammonium hydroxide to form the cavity.

11. The ultrasonic probe according to claim 1 wherein said ultrasonic probe is of a size insertable into the patient's blood vessel and the elongated main body portion has a surface suitable for a sheath to slide on the elongated main body to guide the sheath to a desired location.

12. The ultrasonic probe according to claim 1 wherein the bottom electrode penetrates the backing layer and the top electrode penetrates the acoustic matching layer.

13. The ultrasonic probe according to claim 1 wherein the transducer block has sides and at least one of the bottom and top electrodes extends substantially from one side to another side remote therefrom.

14. A method of making an ultrasonic probe for imaging tissues from inside a patient's body cavity having a wall, the ultrasonic probe having a distal end suitable for inserting into the body cavity, comprising:

(a) forming a generally rectangular transducer block with a backing layer, a transducer layer on said backing layer, a matching layer on said transducer layer, a first electrode to connect electrically a bottom face of the transducer layer to a conductor which is on a first face of the block, a second electrode to connect electrically a top face of the transducer layer remote from the bottom face of the transducer layer to a conductor on another face of the block for activating the transducer layer;

(b) attaching said block to a support slab with the matching layer facing away from the slab, the slab having a transducer-support layer, ferromagnetic material on top of the transducer-support layer, and a substrate layer below said transducer-support layer and ferromagnetic material;

(c) after attaching said block to said slab, etching away a portion of the substrate layer chemically to create a cavity which is defined between said transducer-support layer and unetched material of the substrate layer, said transducer-support layer having been formed to have one or more deformable links supporting the block on a portion of the transducer-support layer such that the block can pivot back and forth on said one or more links at the cavity; and (d) operatively and electrically connecting the substrate-etched slab with the block thereon to an elongated body with a driver proximate to the distal end, thereby forming the ultrasonic probe, the driver being capable of driving the block to pivot back and forth.

15. The method according to claim 14 further comprising forming the transducer block by a process including:

(i) providing a block including said backing layer, said transducer layer and said matching layer, said block having a top surface facing away from backing layer, a bottom surface facing away from the matching layer, and side surfaces encircling said block between the top surface and the bottom surface.

(ii) cutting a first void on the backing layer to reach a bottom face of the transducer layer and cutting a second void on the matching layer to reach a top face of the transducer layer;

(iii) depositing a conductive material on said first and second voids to form said first and second electrodes; and (iv) providing electrically insulating coating on said electrodes such that a portion of each of the first and second electrodes is exposed but not electrically connected to each other, said exposed electrodes being provided for electrical connection to activate the transducer layer.

16. The method according to claim 14 further comprising forming the transducer block by a process including:

(i) providing a large plate of said transducer layer sandwiched between said backing layer and said matching layer, said plate having a top surface on said matching layer, a bottom surface on said backing layer remote from the matching layer, and side surfaces encircling said plate between the top surface and the bottom surface;

(ii) cutting a first set of parallel channels on the backing layer to reach a bottom face of the transducer layer and cutting a second set of channels on the matching layer to reach a top face of the transducer layer;

(iii) depositing a conductive material on said first and second sets of channels;

(iv) dicing the plate perpendicular to the plate's top surface to form blocks each of which having conductive material from a channel of said first set thereby becoming said first electrode and each of the block having conductive material from a channel of said second set thereby becoming said second electrode in the block, each block having corresponding side surfaces; and (v) for each block providing an electrically insulating coating on the block side surfaces such that at least a portion of each of the first and second electrodes is exposed for electrical connection to activate the transducer layer.

17. The method according to claim 14 further comprising etching the transducer-support layer in selected area to form the links.

18. The method according to claim 14 further comprising forming transducer-support layer such that two links are formed each on one side of the transducer block and forming the ferromagnetic material in selected area on the transducer-support layer such that the ferromagnetic material would be located under the transducer block to provide motive force when in a varying magnetic field and on the links to provide electrical activation to the transducer, such that the ferromagnetic material is not electrically continuous between the links.

19. The method according to claim 14 further comprising providing the driver such that all mechanical driving motions for driving the transducer block's pivotal back and forth motion occur proximate to the inserting end of the ultrasonic probe.

20. The method according to claim 14 further comprising electrically connecting an electrical conductor to an electromagnet and the same electrical conductor to the transducer layer such that said electrical conductor while providing electrical current of relatively high voltage and low current activates the transducer layer to emit ultrasonic energy and while providing electrical current of relatively low voltage and high current activates the electromagnet to drive the transducer block's pivotal motion.

21. The method according to claim 20 further comprising connecting a controller circuit to switch electrical current passing through said electrical conductor such that the electromagnet and the transducer layer are not activated simultaneously.

22. The method according to claim 14 wherein the substrate layer is silicon and the method further comprising selectively etching away a portion of the silicon substrate layer with tetramethyl ammonium hydroxide to form the cavity.

23. A method for imaging tissues from inside a patient's body cavity having a wall, comprising:

(a) conducting an electrical current of active voltage through a conductor to a support arm supporting a back and forth pivotable transducer assembly inside a housing surrounding the transducer assembly at an inserting end of an ultrasonic probe to activate a transducer in the transducer assembly to generate an ultrasonic beam; and (b) conducting an electrical current of higher voltage and lower current than the electrical current of step (a) through the same conductor to an electromagnet to drive the transducer assembly to pivot back and forth to swingingly scan the ultrasonic beam in the body cavity to image the wall.

24. The method according to claim 23 further comprising activating the driver and the transducer such that they are not activated simultaneously and when the driver is activated all driving motions that drive the pivotal motion of the transducer assembly occur proximate to the inserting end of the ultrasonic probe.

25. A method of making an ultrasonic probe usable as a guidewire capable of imaging tissues from inside a patient's body cavity having a wall, the ultrasonic probe having an distal end suitable for inserting into the body cavity, comprising:

(a) forming a generally rectangular transducer block with a backing layer, a transducer layer on said backing layer, a matching layer on said transducer layer, a first electrode connecting electrically a bottom face of the transducer layer and a second electrode connecting electrically a top face of the transducer layer remote from the bottom face, the forming process including:

(i) providing a large plate of said backing layer, transducer layer and matching layer, said plate having a top surface remote from backing layer, a bottom surface remote from the matching layer, and side surfaces encircling said plate between the top surface and the bottom surface;

(ii) cutting a first set of parallel channels on the backing layer to reach the bottom face of the transducer layer and curing a second set of channels on the matching layer to reach the top face of the transducer layer;

(iii) depositing a conductive material on said first and second sets of channels;

(iv) dicing the plate on planes perpendicular to the plate's top surface to form blocks each of which having conductive material from a channel of said first set to result in said first electrode and each of the block having conductive material from a channel of said second set to result in said second electrode in the block, each block having corresponding side surfaces; and (v) for each block providing an electrically insulating coating on the block side surfaces such that at least a portion of each of the first and second electrodes is exposed, each on a different side surface for electrical connection to activate the transducer layer; and (b) attaching said block to a support slab with the matching layer facing away from the slab, the slab having a transducer-support layer, ferromagnetic material on top of the transducer-support layer, and a silicon substrate layer below said transducer-support layer and ferromagnetic material;

(c) after attaching said block to said slab, etching away a portion of the silicon substrate layer chemically with tetramethyl ammonium hydroxide to create a cavity which is defined between said transducer-support layer and unetched silicon material of the substrate layer, said transducer-support layer having been formed to have two torsion arms supporting the block on a portion of the transducer-support layer such that the block can pivot back and forth on said support arms at the cavity; and (d) operatively and electrically connecting the substrate-etched slab with the block thereon to an elongated body with a driver proximate to its distal end to form the ultrasonic probe, said elongated body being of a size such that its distal end is insertable into the patient's blood vessel and having a surface effective for guiding a sheath when the sheath is slid thereon, said electrically connecting including electrically connecting an electrical conductive core to an electromagnet and the same electrical conductive core to the transducer layer via one of the links such that the electrical conductive core while providing electrical current of relatively high voltage and low current activates the transducer layer to emit ultrasonic energy and while providing electrical current of relatively low voltage and high current activates the electromagnet to drive the transducer block's pivotal motion, such that the driver is capable of driving the block to pivot back and forth.

* * * * *